(12) United States Patent
Kain et al.

(10) Patent No.: US 10,921,328 B2
(45) Date of Patent: Feb. 16, 2021

(54) BIOMARKERS FOR EARLY DETERMINATION OF A CRITICAL OR LIFE THREATENING RESPONSE TO ILLNESS AND/OR TREATMENT RESPONSE

(71) Applicant: Fio Corporation, Toronto (CA)

(72) Inventors: Kevin Kain, Toronto (CA); W. Conrad Liles, Seattle, WA (US); Laura Erdman, Toronto (CA); Andrea Conroy, Toronto (CA)

(73) Assignee: FIO CORPORATION, Toronto (CA)

( * ) Notice: Subject to any disclaimer, the term of this patent is extended or adjusted under 35 U.S.C. 154(b) by 692 days.

(21) Appl. No.: 14/916,758

(22) PCT Filed: Sep. 5, 2014

(86) PCT No.: PCT/CA2014/050841
§ 371 (c)(1),
(2) Date: Mar. 4, 2016

(87) PCT Pub. No.: WO2015/031996
PCT Pub. Date: Mar. 12, 2015

(65) Prior Publication Data
US 2016/0216274 A1 Jul. 28, 2016

Related U.S. Application Data

(63) Continuation of application No. 14/019,447, filed on Sep. 5, 2013, now abandoned.

(51) Int. Cl.
*G01N 33/68* (2006.01)
(52) U.S. Cl.
CPC ..... *G01N 33/6842* (2013.01); *G01N 2800/50* (2013.01); *G01N 2800/52* (2013.01); *Y02A 50/30* (2018.01)

(58) Field of Classification Search
CPC ................................................ G01N 33/6842
USPC ......................................................... 702/19
See application file for complete search history.

(56) References Cited

U.S. PATENT DOCUMENTS

2011/0008804 A1  1/2011  Kain et al.
2011/0117107 A1  5/2011  Stiles et al.

FOREIGN PATENT DOCUMENTS

CA        2769433 A1      8/2013
WO    WO-2012016333 A1   2/2012

OTHER PUBLICATIONS

Conroy et al (Dec. 2011) "Performance Characteristics of Combinations of Host Biomarkers to Identify Women with Occult Placental Malaira: A Case-Control Study from Malawi," PLos ONE, vol. 6, Issue 12, 7 pages.
International Search Report for PCT/CA2014/050841, dated Nov. 24, 2014, 5 pages.
Written Opinion for PCT/CA2014/050841, dated Nov. 24, 2014, 7 pages.
Baker, "In biomarkers we trust?," Nature Biotechnology, vol. 23, No. 3 (Mar. 2005), 8 pages.
Bast, et al, "Translational Crossroads for Biomarkers," AACR Journals, Clin Cancer Res (Sep. 1, 2005) 6 pages.
Erdman et al, "Combinations of Host Biomarkers Predict Mortality among Ugandan Children with Severe Malaria: A Retrospective Case-Control Study", PLos ONE, vol. 6, Issue 2, (Feb. 2011), 12 pages.
Jain, et al, Plasma IP-10, apoptotic and angiogenic factors associated with fatal cerebral malaria in India, Malaria Journal (2008), 7:83, BioMed Central, 15 pages.
LaBaer, "So, You Want to Look for Biomarkers (Introduction to the Special Biomarkers Issue)", Journal of Proteome Research (2005) 4, 7 pages.
Mankhambo, et al, "The role of angiogenic factors in predicting clinical outcome in severe bacterial infection in Malawian children", Critical Care (2010), 14:R91, 11 pages.
Silver, et al, "Endothelial activation and dysregulation: A common pathway to organ injury in infectious diseases associated with systemic inflammation", Drug Discovery Today: Disease Mechanisms, vol. 4, No. 4, (2007), 8 pages.
Office Action for Canadian Patent Application No. 2,769,433, dated Jan. 9, 2018 (6 pages).
Supplementary European Search Report for European Patent Application No. EP14842541, dated Jun. 14, 2017 (10 pages).

*Primary Examiner* — Jerry Lin
(74) *Attorney, Agent, or Firm* — Goodwin Procter LLP

(57) ABSTRACT

The invention relates to the use of novel biomarkers and biomarker combinations having utility in the early determination of an individual's critical and/or life threatening response to illness and/or in predicting outcome of said illness. The measurement of expression levels of the products of the biomarkers and combinations of biomarkers of the invention have utility in making the determination of an individual's critical and/or life threatening response to illness. In some embodiments, the biomarker and biomarker combinations are agnostic and are independent of the pre-identification and/or determination of the cause or nature of the illness. In some embodiments, the biomarkers and biomarker combinations can be utilized to select treatment and/or monitor the effectiveness of treatment interventions for an individual who has a critical illness.

27 Claims, 14 Drawing Sheets

Figure 1A:
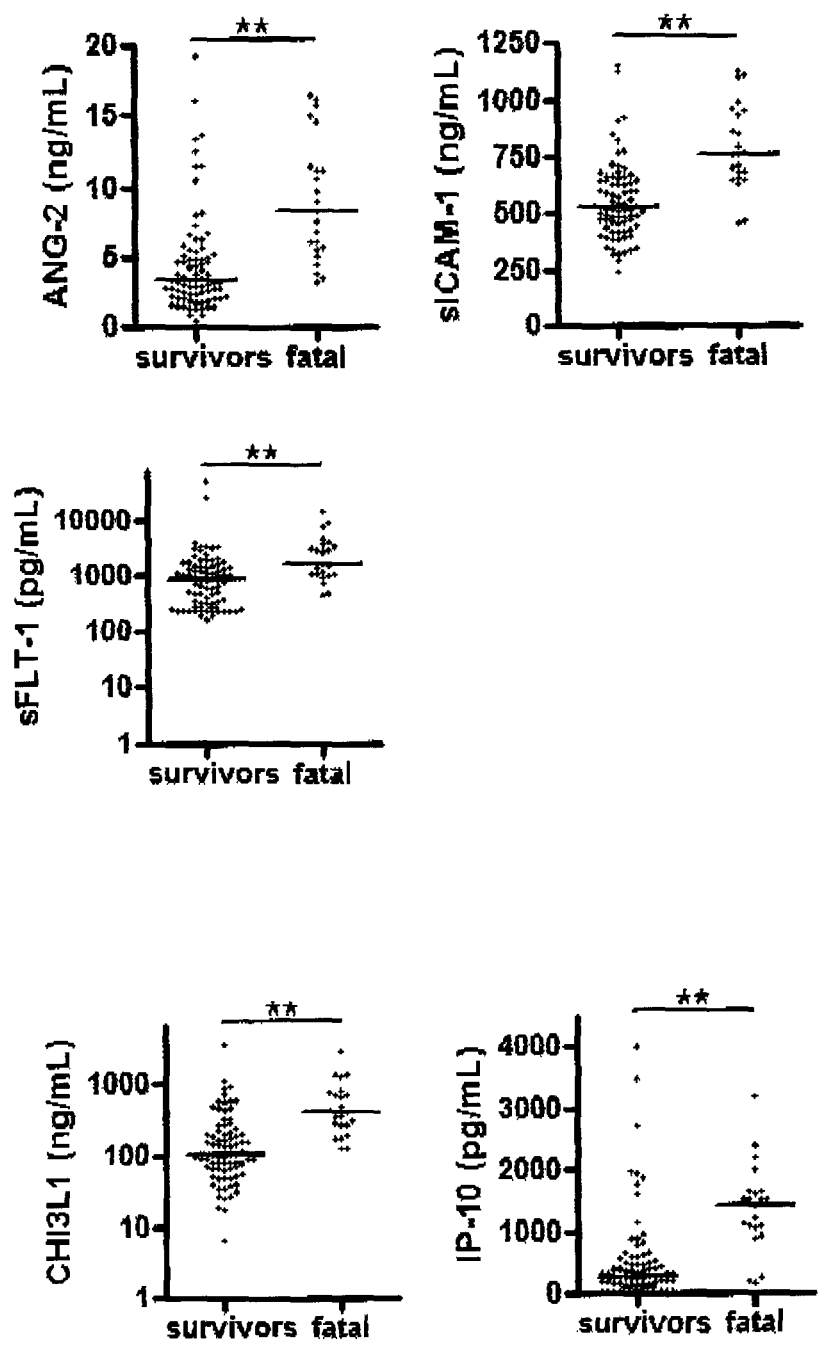
Figure 1A:
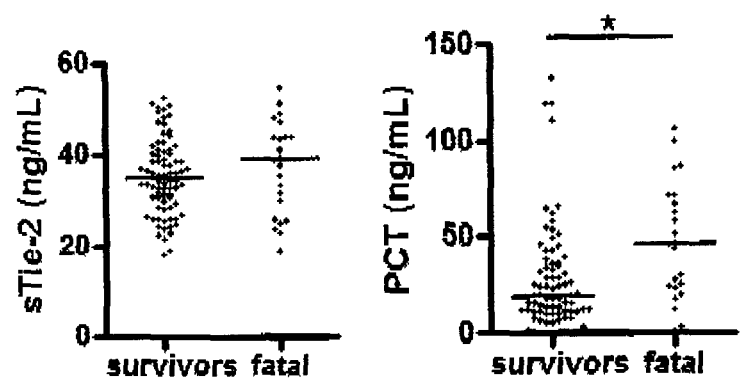

BIOMARKERS FOR EARLY DETERMINATION OF A CRITICAL OR LIFE THREATENING RESPONSE TO ILLNESS AND/OR TREATMENT RESPONSE

CROSS-REFERENCE TO RELATED APPLICATIONS

This application is a national stage filing under 35 U.S.C. § 371 of International Patent Application No. PCT/CA2014/050841, filed Sep. 5, 2014, which claims the benefit of and priority to U.S. patent application Ser. No. 14/019,447, filed Sep. 5, 2013, each of which is hereby incorporated herein by reference in its entirety.

1. FIELD OF THE INVENTION

Encompassed within the scope of the invention is the use of novel biomarkers and biomarker combinations having utility in the early determination of an individual's critical and/or life threatening response to illness and/or in predicting outcome of said illness. In some embodiments, the biomarker and biomarker combinations are agnostic and are independent of the pre-identification and/or determination of the cause or nature of the illness. In some embodiments, the biomarkers and biomarker combinations can be utilized to monitor the effectiveness of treatment interventions for an individual who has a critical illness or to select a treatment intervention which is likely to be effective for the individual, independently of the pre-identification and/or determination of the cause or nature of the illness.

2. BACKGROUND OF THE INVENTION

Diagnosis and Treatment

Diagnosis, in the medical context, is the act or process of identifying or determining the nature and/or cause of an illness by identifying the condition(s) (including the diseases and/or injuries) responsible through evaluation of one or more factors which can include patient history, physical examination, review of symptoms and review of data from one or more laboratory tests. While it is not always possible to identify the exact nature or cause of the illness, differential diagnosis may also be utilized in an attempt to eliminate one or more possible causes in order to select the most likely cause.

Once a diagnosis or differential diagnosis has been made, treatment options are considered, and a treatment strategy chosen. In some cases, treatment may begin before diagnosis has been completed (for example, treatment pending receipt of lab results). In other cases, the cause of the illness may remain elusive, but nevertheless treatment is selected on the basis of the symptoms which the individual presents. When the diagnosis, differential diagnosis, or symptoms are indicative of a condition which has the potential to be critical and/or life threatening, the management strategy may include additional considerations to ensure the best possible clinical outcome including rapid triage, referral, admission to hospital, enhanced monitoring, admission to an intensive care unit, and the like.

The Agnostic Approach to Diagnosis and Treatment

The traditional model of selecting a treatment strategy based solely on the pre-determined origin or cause of the illness has some significant drawbacks. While identifying the cause helps to ensure that the selected course of treatment is disease, injury, or at least symptom specific, it often fails to recognize the importance that the individual's unique response to their condition plays in defining the course and severity of the illness. It also places an emphasis on diagnostic predetermination of disease or illness which may be incompatible with the availability and/or financial burden associated with appropriate diagnostic methods.

The "agnostic" approach to treatment challenges the traditional paradigm of selecting a treatment strategy based on the origin or cause of illness. The agnostic approach is chosen not necessarily because the cause or origin is unknowable (as in the religious context), or because diagnosis cannot be of assistance, but because knowing as early as possible and/or without the benefits of diagnosis whether an individual will respond critically and/or in a life threatening manner to illness can provide a more effective and rapid method to triage and select appropriate treatment tailored to the individual.

Individual's Response to Illness

It is well recognized that not all individuals respond to an illness in the same manner. Many develop only mild and self-limited disease, while a small proportion may progress to a critical and/or life threatening stage. At presentation to medical care, it can be difficult to determine who will do well without intervention, or with only minimal intervention, and who needs admission and specialized management in order to improve clinical outcome. For example, in the case the H1N1 influenza pandemic, it was estimated that approximately 61 million individuals in the United States were infected with H1N1 (during the period from April 2009 to April 2010), but only a small percentage of those cases resulted in death. Of the 61 million individuals infected, approximately 274,000 individuals were admitted for hospitalization (0.449%), and 12,470 thousand deaths occurred (0.012%) (Emerging Infection Programs Data released May 14, 2010 from the Centre for Disease Control; Deaths rounded to the nearest ten. Hospitalizations have been rounded to the nearest thousand and cases have been rounded to the nearest million). Clearly some individuals were more able to fight the H1N1 infection than others.

Despite this diversity of response, it has been difficult, even with retrospective analysis, to determine what specific factors and characteristics contributed to the differential outcome in these individuals. For example, a retrospective study was performed on worldwide data available prior to Jul. 16, 2009 on the 684 deaths reported as of that date (Vaillant, L. et al., Eurosurveillance, Vol. 14, Issue 33, p. 1-6 (2009)) and the age of the patients were reviewed, by country. In that study it was found that while overall most deaths (51%) occurred in the age group of 20-49, the impact of age, and the age group most impacted varied in different countries, making it difficult to draw predictive conclusions.

Another example of an illness which has life threatening potential is sepsis (septicemia). Sepsis is a systemic inflammatory response to a presumed infection, and may result from numerous diverse diseases or etiologies. In some cases severe sepsis may develop wherein the syndrome is also associated with organ dysfunction, hypoperfusion, or hypotension.

Because only a small fraction of individuals with an illness proceed to have a critical and/or life threatening response, an ability to differentiate those individuals who require urgent triage and intensive treatment from those individuals who do not, would be of significant advantage.

Current attempts to selectively treat individuals who are most vulnerable for a life threatening response to an illness occurs by first diagnosis said illness, and then either pre-classifying individuals based on known risk factors (e.g. age, existing co-morbidities and the like) and/or by monitoring individuals for early indications that suggest the illness is proceeding in a life threatening manner. For example, a prospective cohort study conducted in 2 phases at 2 general hospitals in Brazil found that by increased monitoring of in-hospital patents using currently existing measurable indicators for detection specific to sepsis, and providing treatment accordingly, the mortality rate for patients was reduced from 61.7% to 38.2% (Wesphal, G. A., et al. "Reduced mortality after the implementation of a protocol for the early detection of severe sepsis" Journal of Critical Care (2011) 26 p. 76-81).

Nevertheless, reliance on risk factors remains vastly inadequate as a means of selecting individuals who are likely to have a life threatening response (see Vaillant, L. et al. supra), and existing measurable indicators that an individual is having a life threatening response often requires extensive and costly monitoring of patients and can take too long to be of clinical use in managing the patient. Furthermore, relying on diagnosis prior to monitoring or providing treatment can increase costs and cause unnecessary delay. This is problematic, particularly in cases where resources are limited, such as in developing countries, but applies equally to developed countries given the costs associated with critical care.

For example, in the case of H1N1 treatment, Durben et. al. modeled the costs from a societal perspective for the treatment of the Ontario population (assuming no preventative vaccination) and determined a total cost of $1.10 billion dollars with approximately 87 million dollars being allocated to various aspects of hospital care (Durben et al. (2011) "A cost effectiveness analysis of the H1N1 vaccine strategy for Ontario, Canada" Journal of Infectious Diseases and Immunity Vol. 3(3) p. 40-49). The early and accurate identification and stratification of those individuals more likely to have a poor response to the infection could have focused resources on those most likely to benefit from them and away from the majority of infected individuals who recovered well without specific medical intervention. This strategy would presumably have decreased these projected costs quite significantly.

Thus, what is needed in the art is one or more biomarkers which provide greater certainty than current models of an individual's increased risk of progressing to a critical and/or life threatening response to illness, and/or to identify an individual as needing treatment intervention, so as to select and/or modify an appropriate treatment protocol for said individual. Preferably these biomarkers would recognize the increased risk as early as possible so as to allow the greatest potential for treatment intervention. It would also be particularly helpful if the biomarkers were agnostic and had utility irrespective of the illness, so it would be unnecessary to first diagnose the illness. Also, the ability to use one or more biomarkers to monitor the impact of the treatment protocol on the progress of a life threatening response would permit modification of the treatment protocol as necessary would also be of significant benefit.

3. SUMMARY

In one aspect, what is disclosed are biomarkers and biomarker combinations which provide an indication of an individual's response to illness, the severity of that response, and whether they already have, or are progressing to, a critical and/or life threatening form of illness. In another aspect the biomarker and biomarker combinations are capable of providing an early indication of the severity of an individual's response to illness which is not predicated upon first determining the cause or source of the illness. In yet another aspect, what is disclosed are biomarkers and biomarker combinations which can be used prior to, or in place of, diagnosis or differential diagnosis in order to select an appropriate treatment protocol. In yet another aspect, what is disclosed are biomarkers and biomarker combinations which provide an early indication of the impact of the treatment protocol on the individual's risk or progress of their life threatening response.

In another aspect is a composition comprising a collection of two or more antibodies and a suitable buffer, the composition capable of selectively binding to at least two protein biomarkers from a sample isolated from a test individual, where the protein biomarkers are those in Table 1. In another aspect the composition is a composition comprising three or more antibodies and the composition is capable of selectively binding to at least three protein biomarkers from a sample isolated from the test individual, where the protein biomarkers are those in Table 1. In another aspect the composition comprises a collection of two or more antibodies and a suitable buffer, the composition is capable of selectively binding to at least two protein biomarkers from a sample isolated from a test individual, and the protein biomarkers are C5a, VEGF, sFlt-1, CHI3L1, CRP, Ang-like3, FactorD, or IL18bpa). In another aspect the composition comprises a collection of three or more antibodies and a suitable buffer, the composition is capable of selectively binding to at least three protein biomarkers from a sample isolated from a test individual, and the protein biomarkers are C5a, VEGF, sFlt-1, CHI3L1, CRP, Ang-like3, Factor D, or IL18bpa). In yet another aspect, the sample is a whole blood sample, a serum sample or a plasma sample. In another aspect the composition comprises a collection of two or more antibodies and a suitable buffer, the composition is capable of selectively binding to at least two protein biomarkers from a sample isolated from a test individual, and the protein biomarkers are CRP, PCT, CHI3L1, P-Selectin, vWF, Ang3L1, Tie-2, Endoglin, and IL18bpa. In another aspect the composition comprises a collection of three or more antibodies and a suitable buffer, the composition is capable of selectively binding to at least three protein biomarkers from a sample isolated from a test individual, and the protein biomarkers CRP, PCT, CHI3L1, P-Selectin, vWF, Ang3L1, Tie-2, Endoglin, and IL18bpa. In yet another aspect, the sample is a whole blood sample, a serum sample or a plasma sample In some embodiments, the compositions are used to (i) detect and quantify a level of the two or more protein biomarkers in the sample, (ii) compare the quantified level to control levels of the protein biomarkers in a control population, (iii) determine the presence of differential levels for the two or more biomarkers so as to make a determination that the individual is at a significantly increased risk of having a critical and/or life threatening response to illness as compared with the control population. In some embodiments, the detecting and quantifying utilizes one or more devices to transform the sample into data indicative of the levels of each of the two or more protein biomarkers. In some embodiments, the device is an enzyme linked immunoassay which is utilized to transform the sample into data. In some embodiments, the test individual is subjected to a treatment protocol on the basis of the determination in step (iii).

In some embodiments, the control population is an population of individuals having the same illness as the test individual. In some embodiments, the control population is a population of individuals having the same illness as the test individual, and not developing a critical and/or life threatening response to the illness. In some embodiments, the control population is a population of individuals who are normal. In some embodiments, the control population is a population of individuals wherein the majority of members of the control population do not have the same illness as the test individual. In some embodiments, the populations noted above are unbiased populations.

In some embodiments, there is a method of determining the likelihood that a test individual has or will develop a critical and/or life threatening response to illness, where the method includes (i) detecting and quantifying a level of each of two or more protein biomarkers in a sample, where the protein biomarkers are those in Table 1 (ii) comparing the quantified levels of said protein biomarkers to control levels of the protein biomarkers from a control population (iii) determine the presence of differential levels for the two or more biomarkers based on the comparison in step (ii) so as to make a determination that the individual is an increased risk of having a critical and/or life threatening response to illness when compared with the control population.

In some embodiments, the determination is made that the individual is at a significantly increased risk. In some embodiments, the detecting and quantifying of step (i) utilizes one or more devices to transform the sample into data indicative of the levels of each of the two or more protein biomarkers. In some embodiments, the one or more devices is an enzyme linked immunoassay. In some embodiments, the individual is subjected to a treatment protocol on the basis of the determination made. In some embodiments, the control population is an unbiased population of individuals having the same illness as the test individual. In some embodiments, the control population is a population of individuals having the same illness as the test individual, and not developing a critical and/or life threatening response to the illness. In some embodiments, the control population is a population of individuals who are normal. In some embodiments, the control population is a population of individuals wherein the majority of members of the control population do not have the same illness as the test individual.

In some embodiments, there is a method of determining the likelihood that a test individual will develop a critical and/or life threatening response to illness, where the method includes (i) detecting and quantifying a level of each of two or more protein biomarkers in a sample, where the protein biomarkers are those in Table 1 (ii) using the quantified levels of each of the protein biomarkers from the sample in a classifier where the classifier was generated using two populations, a first population who developed a critical and/or life threatening response to illness and a second control population, (iii) making a determination as to whether the quantified levels are indicative of the individual being more similar to the first population or the second control population so as to determine whether the individual is at an increased risk of developing a critical and/or life threatening response to illness.

In some embodiments, the determination is made that the individual is at a significantly increased risk. In some embodiments, the detecting and quantifying of step (i) utilizes one or more devices to transform the sample into data indicative of the levels of each of the two or more protein biomarkers. In some embodiments, the one or more devices is an enzyme linked immunoassay. In some embodiments, the individual is subjected to a treatment protocol on the basis of the determination made. In some embodiments, the second control population is an unbiased population of individuals having the same illness as the test individual. In some embodiments, the second control population is a population of individuals having the same illness as the test individual, and not developing a critical and/or life threatening response to the illness. In some embodiments, the second control population is a population of individuals who are normal. In some embodiments, the second control population is a population of individuals wherein the majority of members of the control population do not have the same illness as the test individual.

In some embodiments, the test individual has not been diagnosed or differentially diagnosed with an illness which has the potential to become critical and/or life threatening prior to use of compositions or methods as disclosed.

In some embodiments, the compositions are used to (i) detect and quantify a level of the two or more protein biomarkers in the sample, (ii) compare the quantified level to control levels of the protein biomarkers in a control population, (iii) determine the presence of differential levels for the two or more biomarkers so as to make a determination that a treatment protocol should be administered to the individual. In some embodiments, the detecting and quantifying utilizes one or more devices to transform the sample into data indicative of the levels of each of the two or more protein biomarkers. In some embodiments, the device is an enzyme linked immunoassay which is utilized to transform the sample into data.

In some embodiments, the control population is a population of individuals having an illness for which it is appropriate to administer the treatment protocol. In some embodiments the control population is a population of individuals for which the administration of the treatment protocol is unnecessary. In some embodiments, the control population is a population of individuals wherein the majority of members of the control population are those to whom it is appropriate to administer the treatment protocol. In some embodiments, the populations noted above are unbiased populations. In some embodiments, the control population is a population of individuals having a bacterial infection which can be treated with antibiotic. In some embodiments, the control population is a population of individuals having a viral infection for which antibiotics would not be effective.

4. BRIEF DESCRIPTION OF THE DRAWINGS

The objects and features of the invention can be better understood with reference to the following detailed description and drawings.

Figure 1B:
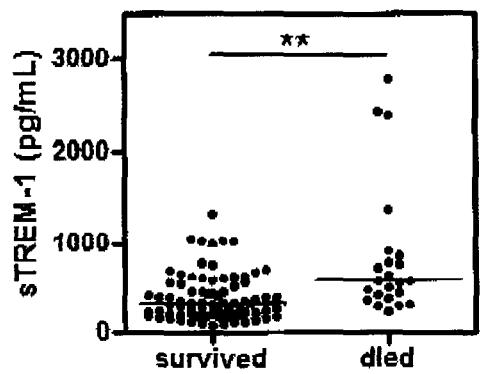

FIGS. 1A and 1B in one embodiment, compares protein biomarker levels isolated from plasma in children who have been diagnosed as having malaria (including individuals who can be subclassified as having either cerebral malaria (CM) or severe malarial anemia (SMA)) and who survived the malaria, as compared with the protein biomarker levels isolated from plasma in children who died from the malaria and demonstrate a statistically significant difference as between the two phenotypic groups. FIG. 1A shows the results from biomarker Ang-2, sICAM-1, sFlt-1, CHI3L1, IP-10, sTie-2, and PCT. FIG. 1B shows the results from biomarker sTREM-1. * indicates a statistical difference in the protein levels with a p value of <0.05. ** indicates p values of <0.01.

Figure 2A:
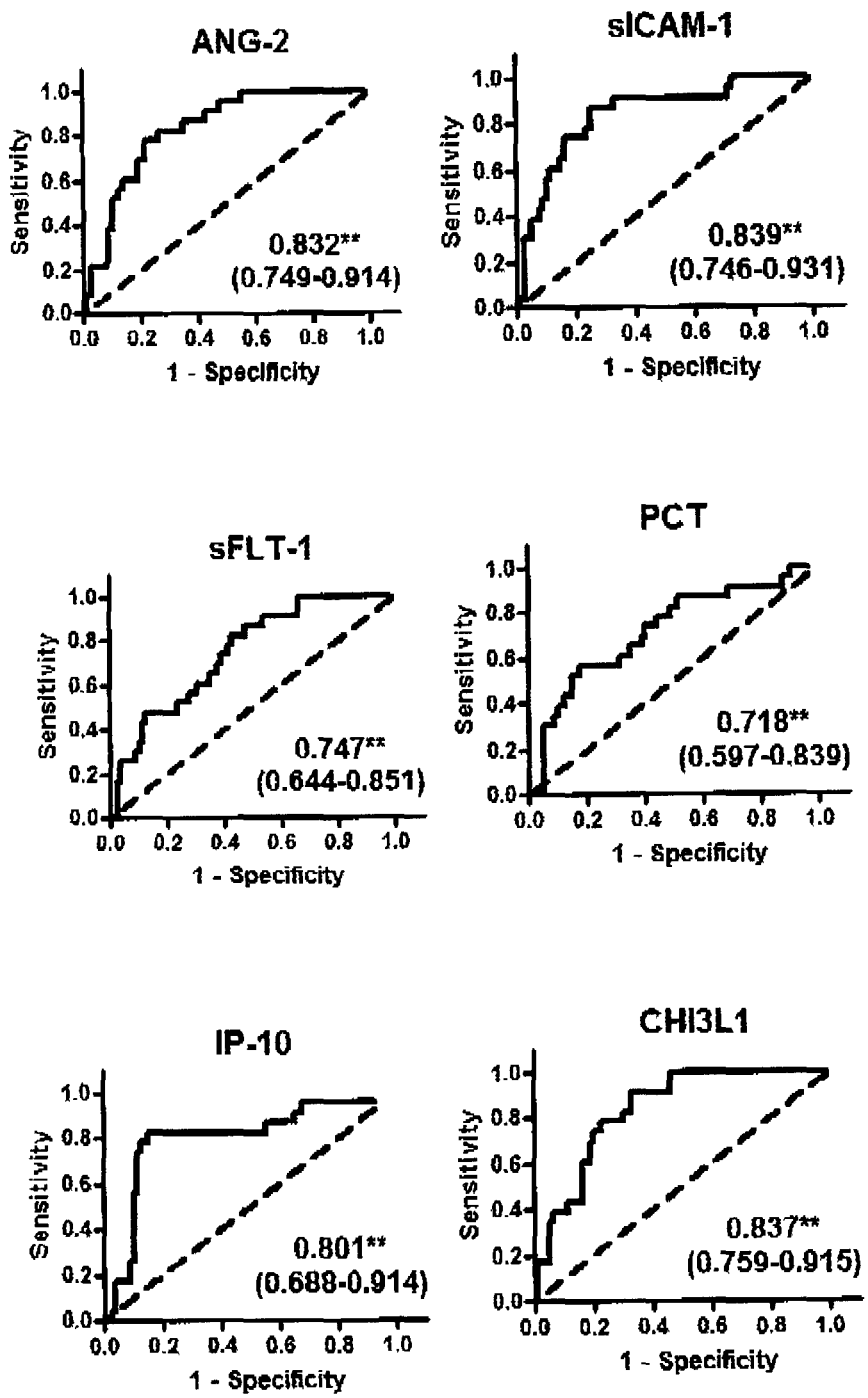

FIG. 2A, in one embodiment, demonstrates the receiver operating characteristic (ROC) curves generated using the selected biomarkers sICAM-1, sFlt-1, Ang-2, PCT, IP-10, sTREM-1, and CHI3L1 to differentiate between fatal and non-fatal malaria. Dashed reference lines represent the ROC curve for a test with no discriminatory ability. Area under the ROC curve is noted in each graph with the 95% confidence interval shown below in parentheses. P values are indicated * p<0.05, ** p<0.01.

Figure 2B:
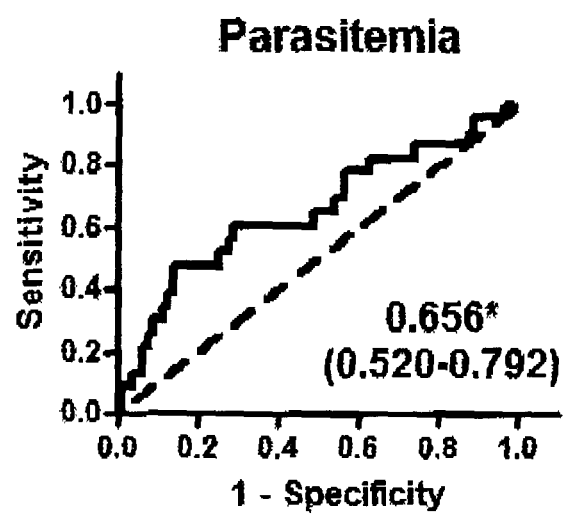

FIG. 2B, in one embodiment, demonstrates the receiver operating characteristic (ROC) curve for parasetimia diagnosis alone. Dashed reference lines represent the ROC curve for a test with no discriminatory ability. Area under the ROC curve is noted in each graph with the 95% confidence interval shown below in parentheses. P values are indicated * p<0.05.

Figure 3:
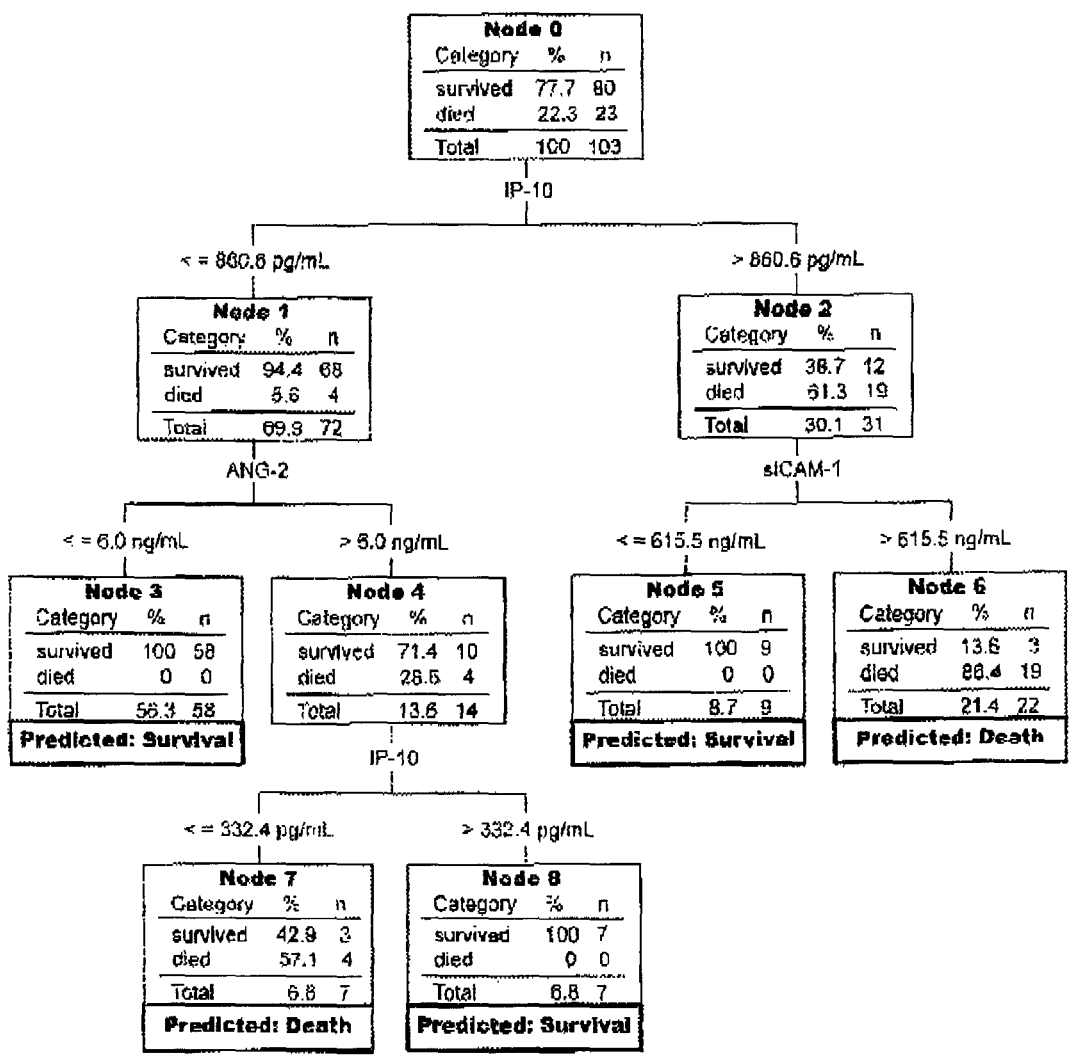

FIG. 3, in one embodiment, demonstrates a classification tree analysis used to predict outcome of severe malaria infection with host biomarkers where six biomarkers were entered into the CRT, and the resulting CRT using IP-10, Ang-2, and sICAM-1 resulted as shown with cut-off points as determined. Prior probabilities of survival and death were specified (94.3% and 5.7% respectively). The cut-points selected by the analysis are indicated between parent and child nodes. Below each terminal node (ie no further branching), the predicted categorization of all patients in that node is indicated. The model yields 100% sensitivity and 92.5% specificity for predicting mortality (cross validated misclassification rate 15.4% with standard error 4.9%).

Figure 4A:
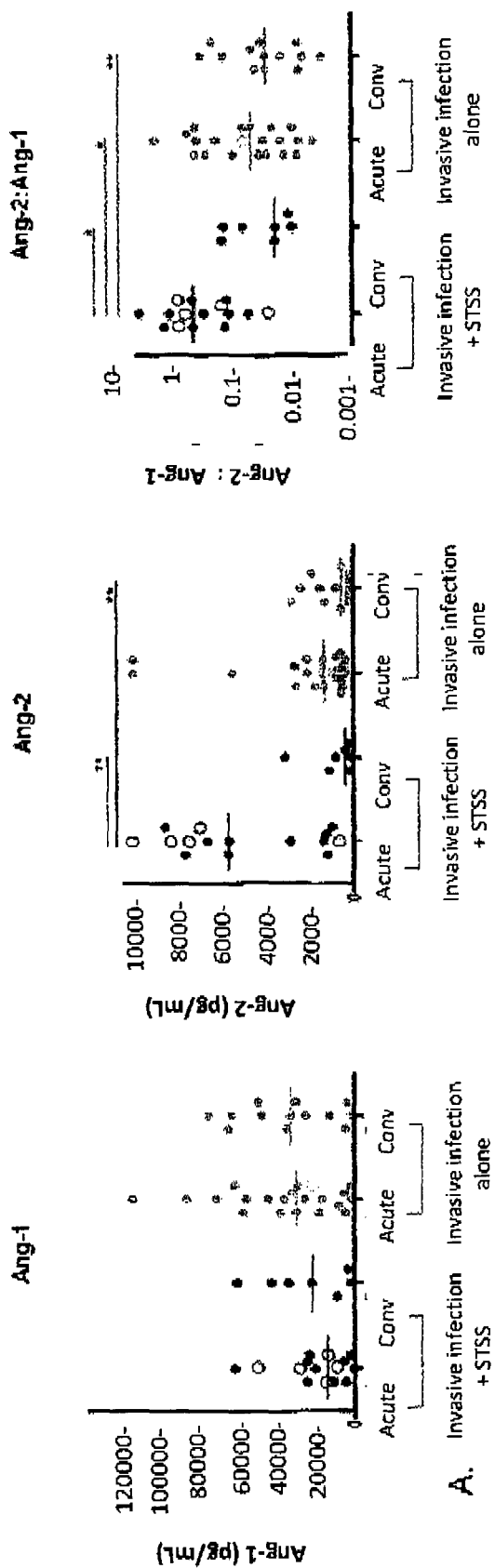

FIG. 4A, in one embodiment, demonstrates the absolute and median concentrations of angiopoietin-1 (Ang-1) and angiopoietin-2 (Ang-2), as well as the ratio between the two (Ang-2:Ang-1 expressed as log base 10) in acute and convalescent plasma from patients with or without STSS. * P<0.05; ** P<0.01.

Figure 4B:
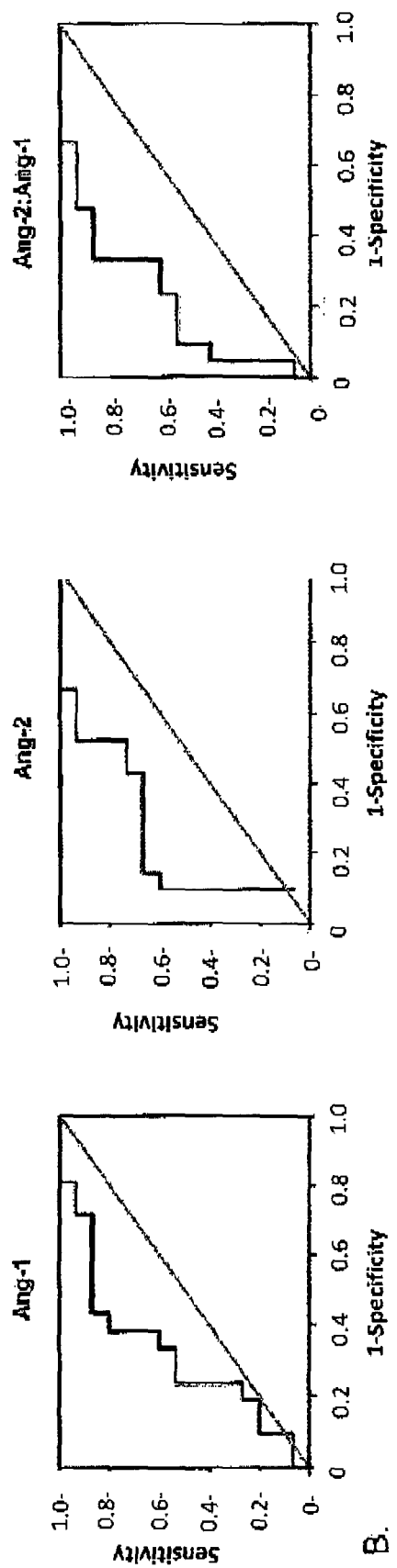

FIG. 4B, in one embodiment, demonstrates the receiver operating characteristic curves for each of Ang-1, Ang-2 and the ratio between the two, comparing patients with STSS in the acute phase of illness to those without STSS, also in the acute phase of illness.

Figure 5:
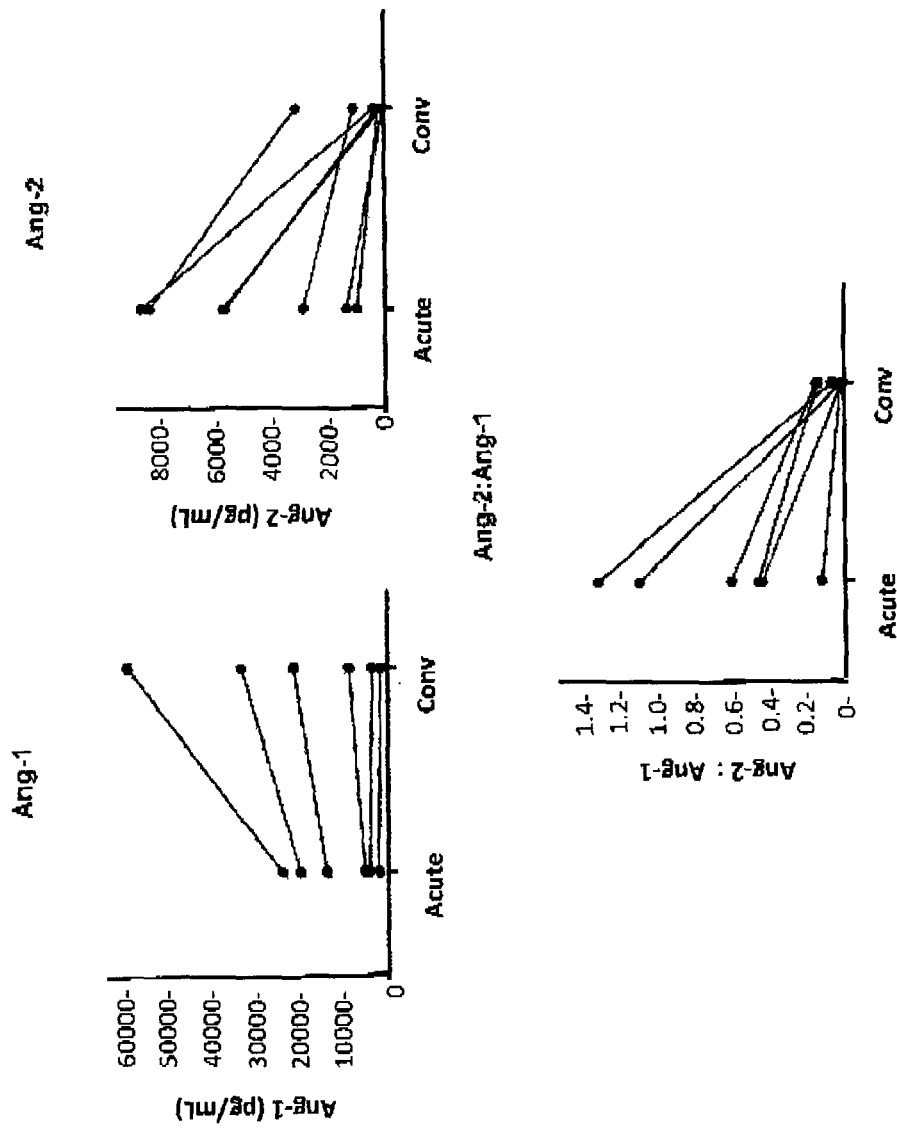

FIG. 5, in one embodiment, shows Angiopoietin-1 and -2 (Ang-1 and Ang-2) concentrations, and the ratio between the two (Ang-2:Ang-1), in matched acute and convalescent plasma samples from patients with invasive Group A streptococcal infection and STSS.

Figure 6:
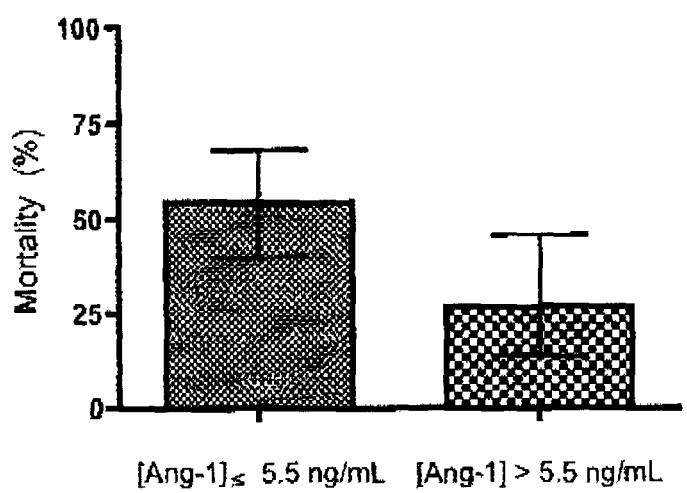
Figure 6:
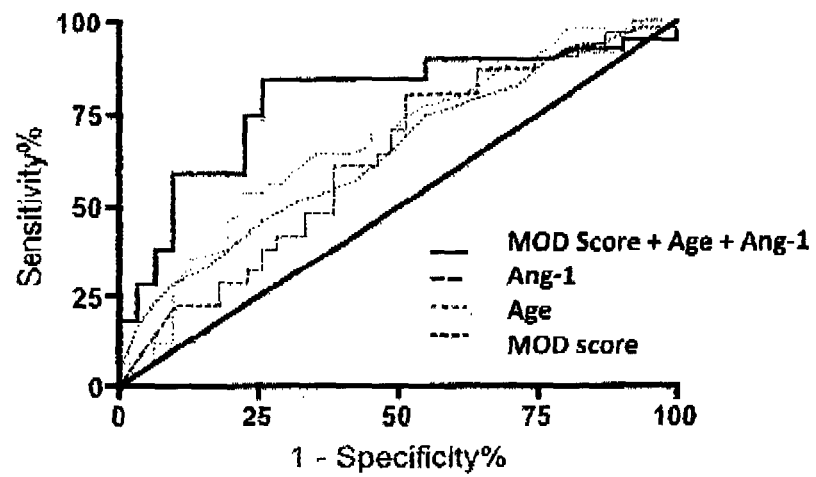

FIG. 6A, in one embodiment, is a histogram showing the relationship between mortality (%) and measured Ang-1 levels on admission.

FIG. 6B in one embodiment, shows a receiver operating characteristic (ROC) curve illustrating added sensitivity and specificity in predicting 28-day mortality when comparing plasma Ang-1 levels, MOD score or age with the combination of the three variables.

Figure 7A:
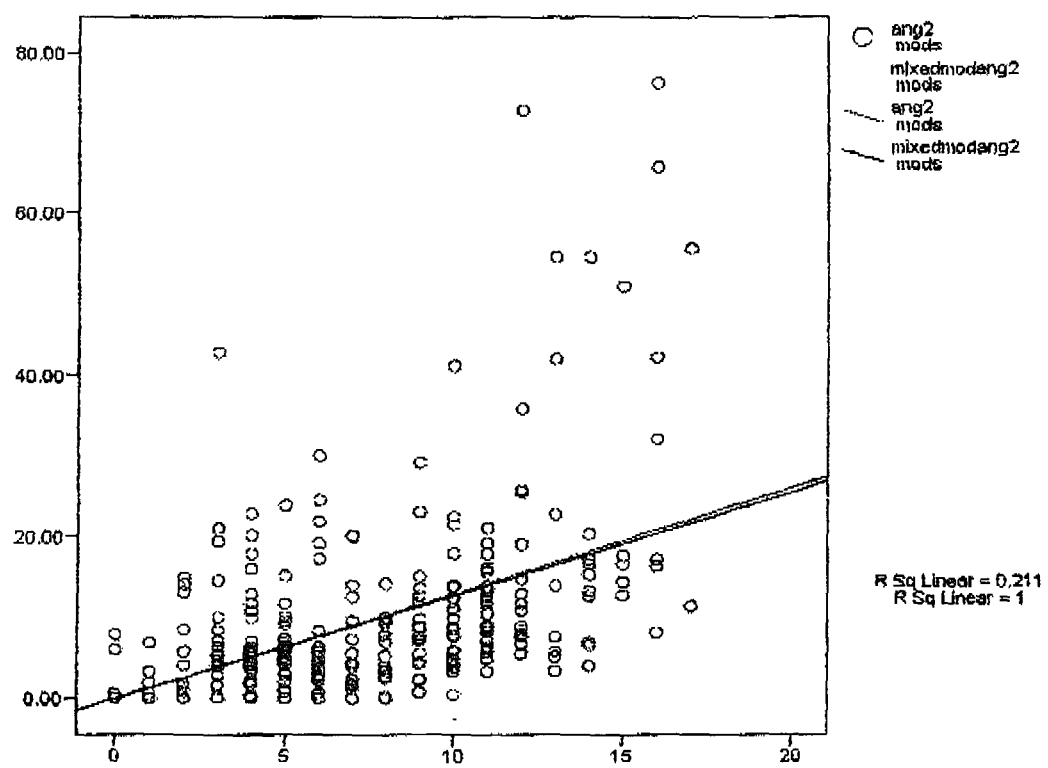

FIG. 7A, in one embodiment, shows the comparison of Ang-2 levels with MOD score as predictors of mortality in patients with severe sepsis.

Figure 7B:
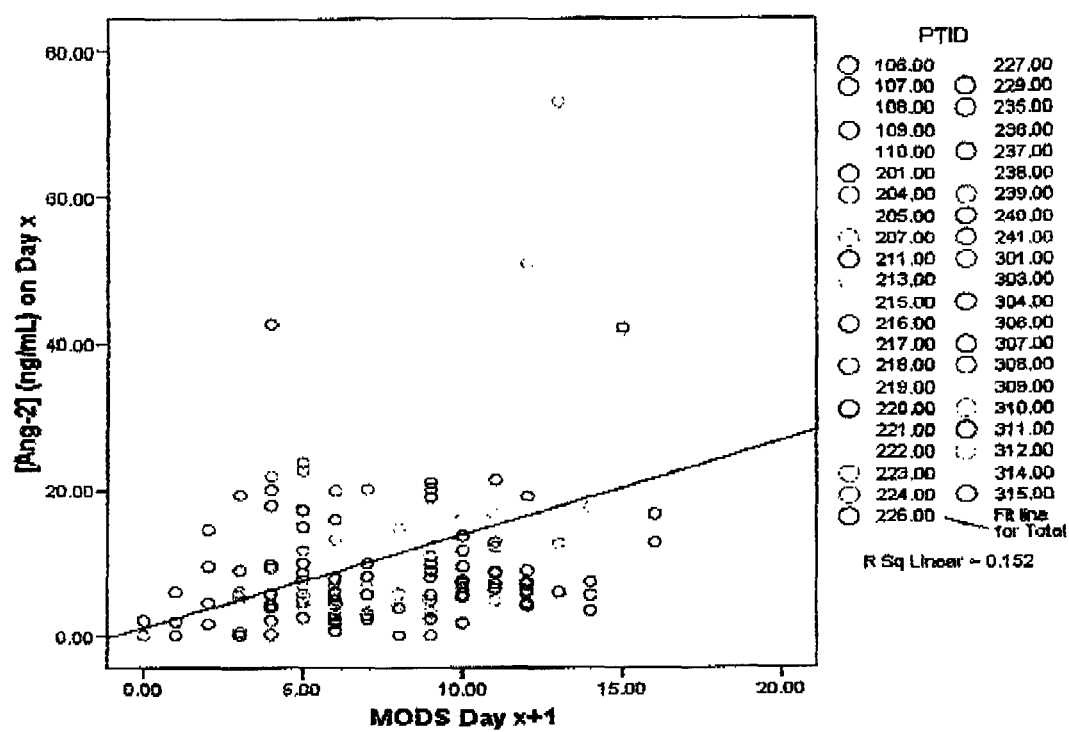

FIG. 7B, in one embodiment, shows the comparison of Ang-2 levels taken one day prior to assessing the MOD score in patients with severe sepsis.

Figure 8A:
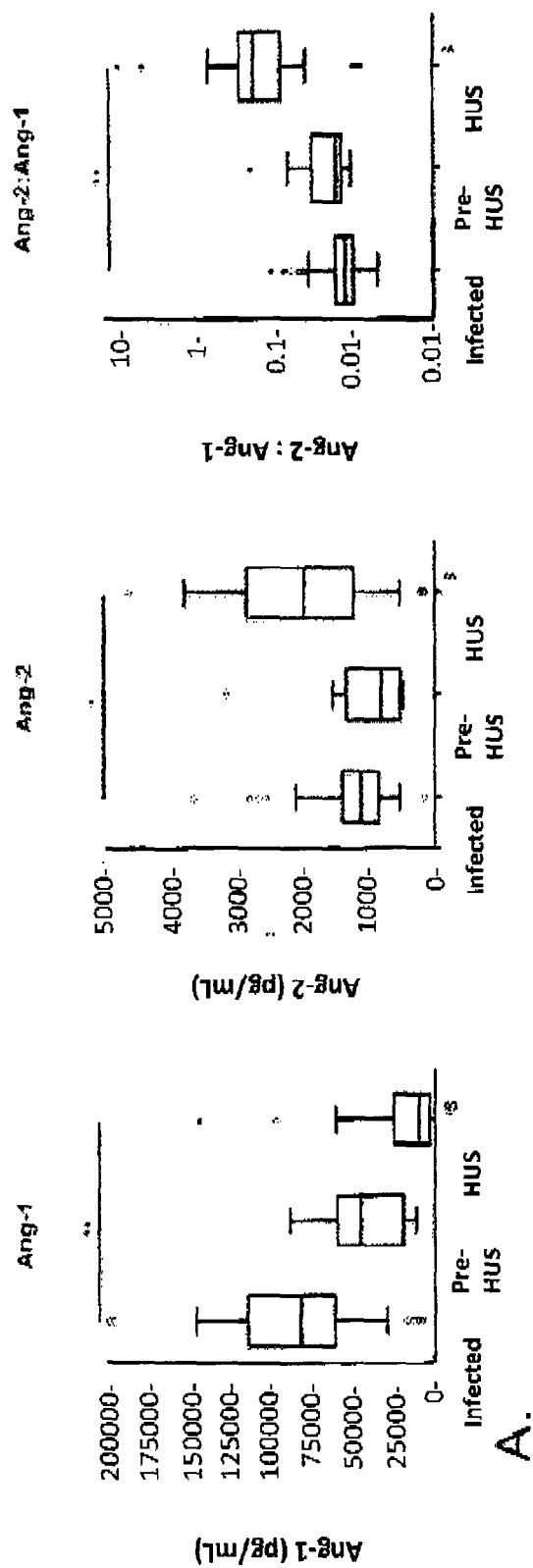

FIG. 8A, in one embodiment, shows the levels of Angiopoietin-1 (Ang-1), Angiopoietin-2 (Ang-2) and the Ang-2:Ang-1 ratio in children with uncomplicated *E. coli* O157:H7 infection (infected), children prior to the diagnosis of HUS (pre-HUS), and children demonstrating HUS at the time of diagnosis (HUS). *p<0.05, **p<0.01 unfilled circles indicate outliers (1.5× interquartile range [IQR], filled circles indicate extreme outliers (3×IQR).

Figure 8B:
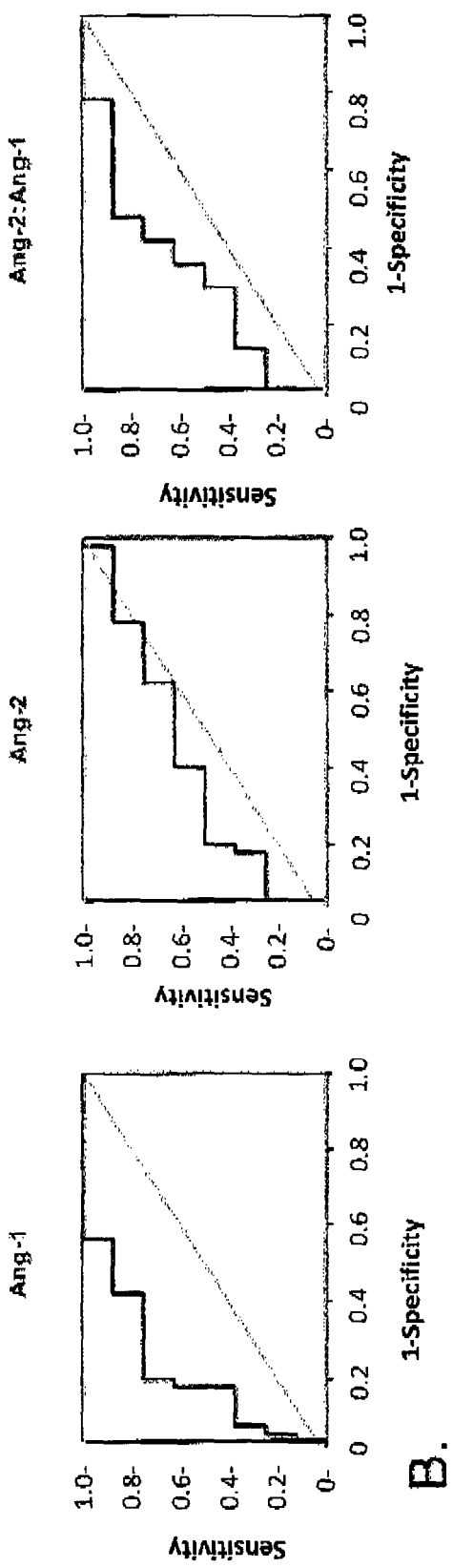

FIG. 8B, in one embodiment, shows Receiver Operating Characteristic (ROC) curves for Ang-1, Ang-2 and Ang-1:Ang-2 ratio as comparing children with uncomplicated infection and those with the pre-HUS phase of illness, with the null hypothesis being that the area under the curve is 0.5 p=0.01 for Ang-1.

Figure 9:
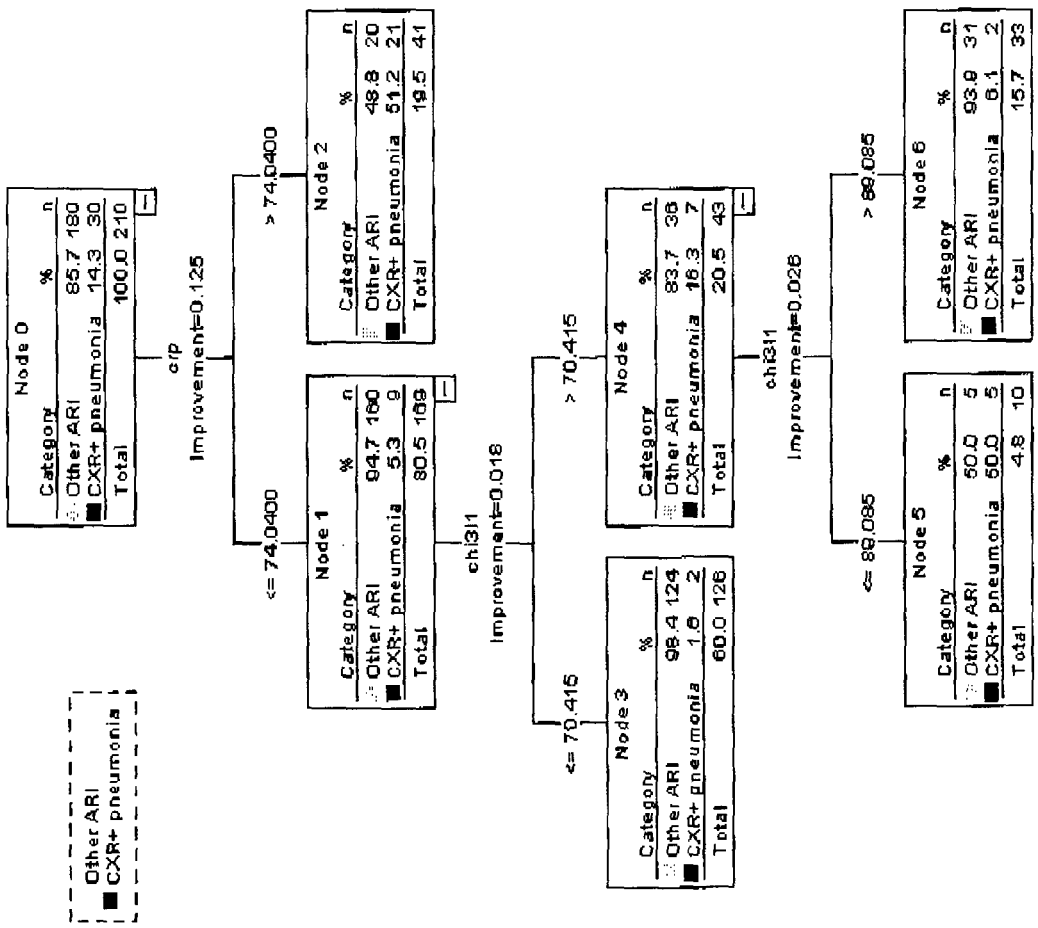

FIG. 9, in one embodiment, shows the CRT analysis of Model 1 of Example 15, from Table 10, wherein the ability of biomarkers CRP, Endoglin and P-selectin 1 to differentiate between children having pneumonia (as confirmed by chest x-ray) and children characterized as having "clinical" pneumonia pursuant to WHO standards, but not having pneumonia in accordance with chest x-ray criteria is shown, as is the incremental benefits of each biomarker when layered onto the decision tree of the previous biomarker.

5. DETAILED DESCRIPTION

5.1 Definitions

The following definitions are provided for specific terms which are used in the following written description.

As used herein, the "amino terminal region of a polypeptide" refers to the polypeptide sequence of a protein biomarker. As used herein, the "amino terminal region" refers to a consecutive, or nearly consecutive stretch of amino acids located near the amino terminus of a polypeptide and is not shorter than 3 amino acids in length and not longer than 350 amino acids in length. Other possible lengths of the "amino terminal" region of a polypeptide include but are not limited to 5, 10, 20, 25, 50, 100 and 200 amino acids.

The term "antibody" encompasses monoclonal and polyclonal antibodies and also encompasses antigen-binding fragments of an antibody. The term "antigen-binding fragment" of an antibody (or simply "antibody portion," or "antibody fragment"), as used herein, refers to one or more fragments of a full-length antibody that retain the ability to specifically bind to a polypeptide encoded by one of the genes of a biomarker of the invention. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The antibody can be monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

As used herein an "array" contemplates a set of protein biomarkers, or antibodies complementary to protein biomarkers, or combinations thereof immobilized to a support. An array can also include fragments of protein biomarkers or fragments of antibodies immobilized to a support wherein the fragment still allows the selective binding of the protein or antibody fragment to its complementary binding partner.

As used herein, the "carboxy terminal region of a polypeptide" refers to the polypeptide sequences of a protein biomarker. As used herein, the "carboxy terminal region" refers to a consecutive, or nearly consecutive stretch of amino acids located near the carboxy terminus of a polypeptide and is not shorter than 3 amino acids in length and not longer than 350 amino acids in length. Other possible lengths of the "amino terminal" region of a polypeptide include but are not limited to 5, 10, 20, 25, 50, 100 and 200 amino acids. The "carboxy terminal" region does not normally include the polyA tail, if one is present in the protein biomarker.

As used herein, the term "classifier" includes a mathematical model generated on its ability to differentiate between at least two different traits with respect to an individual's response to illness. Classifiers can include logistic regression, classification and/or regression tree analysis, or other known mathematical models, and are generated using at least two populations wherein the phenotype of the populations is known. In some embodiments, a first population has been confirmed as demonstrating a critical and/or life threatening response to illness, and the second population is a control population as defined herein. The classifier, so generated, can be used with data from a test individual to generate a numerical output which is indicative of whether the individual is at risk of developing a critical and/or life threatening response to illness, (or is already developing a critical and/or life threatening response to illness), or not.

As used herein the term "complementary binding partner" includes a compound which selectively binds to a protein biomarker and includes nucleic acid aptamers, peptide aptamers, a peptibody, a mimetic, an inhibitor, and any compound that binds to the protein biomarker in vivo, an antibody including a monoclonal and/or polyclonal antibody.

As used herein the term "control population" is considered in reference to the test individual since the levels of the biomarker and biomarker combinations in the test individual must be compared to levels in the control population to determine the likelihood of the test individual having a critical and/or life threatening response, and/or to predict the outcome of the response. Control populations can either be negative control populations or positive control populations. In some embodiments, the control population is a negative control population, the test individual has been diagnosed with an illness, and the control population is a population of individuals who have had the illness of the test individual and have not developed a critical or life threatening response. In some embodiments, the test individual has been diagnosed with an illness and the control population is a population of normal individuals. In some embodiments, the test individual has been diagnosed with an illness and the control population is an unbiased population of individuals with said illness. In some embodiments, the control population is a positive control population, the test individual has been diagnosed with an illness, and the control population is a population of individuals who have had the illness and have developed a critical or life threatening response. In any of the above embodiments, the control population may be an unbiased population.

In some embodiments, the utility of the biomarkers and biomarker combinations is independent of the cause or source of the illness of the test individual. Control populations can still either be negative control populations or positive control populations. In some embodiments the test individual has not been diagnosed and/or differentially diagnosed with an illness prior to testing the biomarker and/or biomarker combinations. In some embodiments, the individual has not been diagnosed and/or differentially diagnosed with an illness that can be critical and/or life threatening prior to testing. In some embodiments, the control population is a negative control population of individuals who have had an illness and have not developed a critical and/or life threatening response. In these embodiments, the illness does not have to be the same as the illness of the test individual (if the illness had been diagnosed and/or differentially diagnosed). In some embodiments, none of the members of the control population have had the same illness as the test individual. In yet other embodiments, the majority of the members of the control population have not had the same illness as the test individual. In yet other embodiments 20%, 30%, 40%, 50%, 60%, 70%, 80%, 90% or more of the control population does not have the same illness as the test individual. In yet other embodiments 20%, 30%, 40%, 50%, 60%, 70%, 80%, 90% or more of the control population has the same illness as the test individual. In some embodiments, the test individual has not been diagnosed with an illness prior to testing the biomarker and/or biomarker combinations and the control population is a population of normal individuals. In some embodiments, the test individual has not been diagnosed with an illness prior to testing, and the control population is a positive control population of individuals who have had an illness and have developed a critical or life threatening response to said illness. In some embodiments, none of the members of the control population have had the same illness as the test individual. In yet other embodiments, the majority of the members of the control population have not had the same illness as the test individual. In yet other embodiments 20%, 30%, 40%, 50%, 60%, 70%, 80%, 90% or more of the control population does not have the same illness as the test individual. In yet other embodiments 20%, 30%, 40%, 50%, 60%, 70%, 80%, 90% or more of the control population has the same illness as the test individual. In yet other embodiments, none of the members of the control population have been diagnosed and/or differentially diagnosed with an illness which is critical and/or life threatening. In yet other embodiments, a majority of the members of the control population have not been diagnosed and/or differentially diagnosed with an illness which is critical and/or life threatening. In yet other embodiments 20%, 30%, 40%, 50%, 60%, 70%, 80%, 90% or more of the control population has not been diagnosed or differentially diagnosed with an illness which is critical and/or life threatening. In yet other embodiments, the control population is a population of individuals who have not been diagnosed and/or differentially diagnosed with an illness which can be critical and/or life threatening. In yet other embodiments, the control population is a population of individuals who have not been diagnosed and/or differentially diagnosed with any illness which is likely to be critical and/or life threatening. In some embodiments, the control population is selected from a region or geographic area comparable with the test subjects and the status of the control population with respect to the critical and/or life threatening illness is determined on the basis of the illnesses that are indigenous to that region or geographic area. In any of the above embodiments, the control population may be an unbiased population.

As used herein "diagnosis" refers to the act or process of identifying or determining the nature and/or cause of an illness by identifying the condition(s) (including the diseases and/or injuries) responsible through evaluation of one or more factors which can include patient history, physical examination, review of symptoms and review of data from one or more laboratory tests.

As used herein "diagnosed with an illness" refers to having confirmed the nature and/or cause of the illness by identifying the agent, disease, or injury responsible for one or more of the symptoms exhibited by said individual, and/or having utilized the diagnostic test(s) and/or benchmarks that are considered the most appropriate tests to be applied to diagnose said illness available under optimum conditions, as defined by conditions that exist in a typical North American hospital, and that have been adopted by as the "gold standard" test for such hospital in determining such illness.

As used herein "differentially diagnosed with an illness" refers to having narrowed down the nature and/or cause of the illness sufficiently to ensure that the patient will receive the same treatment that the patient would have received if the nature and/or cause of the illness was known with certainty, or had been diagnosed utilizing the diagnostic test(s) and/or benchmarks that are considered the most appropriate tests to be applied to diagnose said illness available under optimum conditions, as defined by conditions that exist in a typical North American hospital, and that have been adopted by as the "gold standard" test for such hospital in determining such illness.

As used herein, "illness" refers to a condition which has as one possible outcome a critical and/or life threatening outcome, including death. In some embodiments, illness encompasses disorders of endothelial cell function. In some embodiments, illness is one which results from an infection such as a parasitic infection, a viral infection, a bacterial infection, and/or results from bioactive molecules including microbial toxins. In some embodiments illness includes conditions wherein one of the causes of the condition is a significant burn or physical trauma. In other embodiments illness includes exposure to a biothreat agent such as anthrax. In other embodiments illness includes exposure to agents which can cause acute lung injury, such as smoke. In other embodiments an illness can include disease caused by weaponized microbes and/or biothreat agents, in some embodiments which cannot be diagnosed using traditional diagnosis techniques. For example, the virulence factor or toxin of the microbe and/or biothreat agent has been modified and inserted into a harmless carrier bacteria, virus or other carrier agent (Trojan horse effect). Examples of illnesses include but are not restricted to pneumonias and lower respiratory tract infections, influenza, E. coli infections and its complications such as hemolytic uremic syndrome, bacteremias, rickettsial infections, salmonellosis, streptococcal infections, staphylococcus infections, malaria, sepsis, Dengue fever, west nile virus, toxic shock syndrome, leptospirosis, agents causing viral hemorrhagic fever (e.g. Ebola, Marburg), and microbes or biothreat agents, including those that have been altered to obscure traditional diagnosis.

"Differential levels" refers to protein biomarker levels which demonstrate a statistically significant difference in the level when compared with the levels of the protein biomarker in a control population, wherein the difference is at least 10% or more, for example, 20%, 30%, 40%, or 50%, 60%, 70%, 80%, 90% or more or 1.5 fold, 2 fold, 2.5 fold, 3.0 fold, 3.5 fold, or more in protein levels relative to the levels in a control population.

Differentially increased levels" refers to protein biomarker levels which demonstrate a statistically significant increased level when compared with the levels of the protein biomarker in a control population, wherein the increase in levels is at least 10% or more, for example, 20%, 30%, 40%, or 50%, 60%, 70%, 80%, 90% or more or 1.5 fold, 2 fold, 2.5 fold, 3.0 fold, 3.5 fold, or more increase in protein levels relative to the levels in a control population.

"Differentially decreased levels" refers to protein biomarker levels which demonstrate a statistically significant decreased level when compared with the levels of the protein biomarker in a control population, wherein the decrease in levels is at least 10% or more, for example, 20%, 30%, 40%, or 50%, 60%, 70%, 80%, 90% or more or 1.5 fold, 2 fold, 2.5 fold, 3.0 fold, 3.5 fold, or more decrease in protein levels relative to the levels in a control population.

As used herein "an individual's response to illness" indicates an individual's ability to garner resources to control and/or battle the illness and determines the course of the illness within the individual. The individual's response to illness can be influenced by their innate and acquired immune response, genetic background, medical history, health status, age, sex, and pre-existing or co-existing illnesses and/or treatments. In addition, the course of the illness is also affected by the treatment protocol applied for the illness itself. Irrespective of the specific factors which influence the individual's response to illness, the response impacts the course of the illness in that individual.

As used herein "a critical and/or life threatening response to illness" is indicative of an individual's response to the illness such that the individual is at an increased risk of death as compared with the risk of death in an unbiased population of individuals who suffer the illness. In some embodiments the increased risk of death is a "significantly increased risk" which means that the increase in risk as compared to an unbiased population of individuals having the illness is greater than 50%, 60%, 70%, 80%, 85%, 90%, 95% or more.

As used herein, the "internal region of a polypeptide" refers to the polypeptide sequences of a protein biomarker. As used herein, the "internal region" refers to a consecutive, or nearly consecutive stretch of amino acids located within the internal region of a polypeptide and is not shorter than 3 amino acids in length and not longer than 350 amino acids in length. Other possible lengths of the "internal" region of a polypeptide include but are not limited to 5, 10, 20, 25, 50, 100 and 200 amino acids.

As used herein, "normal" refers to an individual, a group of individuals, or a population of individuals who have not shown any symptoms of illness as defined herein and/or do not have an illness.

As used herein, "patient" or "individual" refers to a human.

As used herein, "protein biomarker" refers to the form of the protein, including fragments, which are expressed and potentially processed and exist in sufficient quantity and for sufficient time so as to be capable of being measured in humans using a compound which selectively binds to the protein. Biomarkers may be capable of being used individually, or in combination with other biomarkers, additively or synergistically to provide information as to an individual's response to illness. As used herein "protein biomarker fragments" may include the "amino terminal region of a polypeptide", the "carboxy terminal" region of a polypeptide" or the "internal polypeptide region of a polypeptide"

As used herein, the terms "purified" in the context of a protein biomarker and/or an complementary binding partner (e.g., a peptide, polypeptide, protein or antibody) refers to a compound which is substantially free of cellular material and in some embodiments, substantially free of heterologous agents (i.e., contaminating proteins) from the cells or tissue source from which it is derived, or substantially free of chemical precursors or other chemicals when chemically synthesized. The language "substantially free of cellular material" includes preparations of a proteins in which the proteins are separated from cellular components of the cells from which it is isolated or recombinantly produced. Thus, a compound that is substantially free of cellular material includes preparations of a compounds having less than about 30%, 20%, 10%, or 5% (by dry weight) of heterologous proteins (e.g., protein, polypeptide, peptide, or antibody; also referred to as a "contaminating protein"). When the compound is recombinantly produced, it is also preferably substantially free of culture medium, i.e., culture medium represents less than about 20%, 10%, or 5% of the volume of the protein preparation. When the compound is produced by chemical synthesis, it is preferably substantially free of chemical precursors or other chemicals, i.e., it is separated from chemical precursors or other chemicals which are involved in the synthesis of the compound. Accordingly, such preparations of a compound have less than about 30%, 20%, 10%, 5% (by dry weight) of chemical precursors or compounds other than the compound of interest.

As used herein, the term "selectively binds" refers to the specific interaction between a protein biomarker and complementary binding partner which is able to interact with the protein biomarker in specific manner, and preferentially to other proteins. Selective binding of a protein biomarker and a complementary binding partner and includes the specific interaction of an antibody with a protein biomarker, including the binding of a monoclonal antibody and/or a polyclonal antibody to a protein biomarker preferentially in comparison to non-specific binding. Selective binding can also include binding between the protein biomarker and a nucleic acid or peptide aptamer, a peptibody, or the like. For example, a region, portion or structure of a first protein molecule recognizes and binds to a region, portion or structure on a second protein molecule preferentially to the binding of a non-specific third protein. "Selective binding", "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As used herein, the term "suspected illness" means an illness which has not been diagnosed and/or differentially diagnosed.

As used herein, the term "a therapeutic protocol" or "treatment protocol", refers to a treatment and/or monitoring strategy which an individual is subjected to, and can be as a result of traditional diagnosis, differential diagnosis, identification of symptoms and/or as a result of use of the protein biomarkers of the invention and can include the application of one or more drug therapies or strategies, medical monitoring which can include increased nursing care, admission to hospital or clinic, admission to an intensive care unit, and or combinations thereof.

By "an unbiased population" as used herein is meant a population of individuals who have a specific illness, but have not been pre-selected on the basis of one or more known risk factors for response to the specific illness (for example, age, sex, existing co-morbidities and the like).

As used herein, "a plurality of" or "a set of" refers to more than two, for example, 3 or more, 4 or more, 5 or more, 6 or more, 7 or more, 8 or more, 9 or more 10 or more etc.

As used herein, the terms "treat", "treatment" and "treating" refer to the reduction or amelioration of the progression, severity and/or duration of episodes and/or symptoms of illness.

5.2 Detailed Summary

We have reviewed various illnesses, each of distinctly different etiologies, which nevertheless have in common the potential to progress to a stage which is critical and/or life threatening. Another commonality amongst these illnesses is the fact that not all individuals, despite being properly diagnosed, progress to the critical and/or life threatening form of the illness. Although it has been known that the individual response to illness plays a significant role in disease progression, it has been difficult to accurately predict which individuals will demonstrate a critical and/or life threatening response, even once the illness has been diagnosed. We have surprisingly identified certain proteins biomarkers, many of which are involved in endothelial activation and/or inflammation, that are found circulating in the blood of individuals who progress to the critical and/or life threatening stage of illness at different levels than the biomarkers are found in individuals who will not demonstrate a critical and/or life threatening response to illness. The biomarkers are often found at different levels even in the very early stages of illness, and often before other known indicators of disease severity can be measured. More surprisingly, we have found that these biomarkers have utility across a diverse group of illnesses suggesting that these biomarkers have utility even if the individual has not yet been diagnosed or differentially diagnosed with a specific illness, making the application of these biomarker particularly useful in situations where: diagnosis is not possible (such as in cases of weaponized microbes or biothreat agents which have been designed to prevent identification), diagnosis may be too costly (such as in developing worlds), diagnosis can delay appropriate treatment, or diagnosis results in overabundance of treatment. As such, we have identified proteins that represent early indicators that an individual is unable to respond effectively to illness and will progress to a critical and/or life threatening stage of illness. Because these proteins are differentially found across such diverse diseases, they have the ability to be used apriori to diagnosis allowing more timely and cost effective interventions than would otherwise be available.

The practice of the present invention employs, in-part conventional techniques of protein chemistry and molecular biology which are within the skill of the art. Such techniques are explained fully in the literature. See, e.g., Sambrook, Fritsch & Maniatis, 1989, *Molecular Cloning: A Laboratory Manual*, Second Edition; Oligonucleotide Synthesis (M. J. Gait, ed., 1984); *Nucleic Acid Hybridization* (B. D. Harnes & S. J. Higgins, eds., 1984); *A Practical Guide to Molecular Cloning* (B. Perbal, 1984); and a series, *Methods in Enzymology* (Academic Press, Inc.); *Short Protocols In Molecular Biology*, (Ausubel et al., ed., 1995). All patents, patent applications, and publications mentioned herein, both supra and infra, are hereby incorporated by reference in their entireties.

5.3 Control and Test Samples

In some embodiments, all that is required is a drop of blood. This drop of blood can be obtained, for example, from a simple pinprick. In some embodiments, any amount of blood is collected that is sufficient to detect the expression of one, two, three, four, five, six, seven or more of the genes in Table 1. In some embodiments, the amount of blood that is collected is 1 ul or less, 0.5 ul or less, 0.1 ul or less, or 0.01 ul or less. In some embodiments more blood is available and in some embodiments, more blood can be used to effect the methods of the present invention. As such, in various specific embodiments, 0.001 ml, 0.005 ml, 0.01 ml, 0.05 ml, 0.1 ml, 0.15 ml, 0.2 ml, 0.25 ml, 0.5 ml, 0.75 ml, 1 ml, 1.5 ml, 2 ml, 3 ml, 4 ml, 5 ml, 10 ml, 15 ml or more of blood is collected from a subject. In another embodiment, 0.001 ml to 15 ml, 0.01 ml to 10 ml, 0.1 ml to 10 ml, 0.1 ml to 5 ml, 1 to 5 ml of blood is collected from a subject.

In some embodiments, whole blood is utilized. In some embodiments of the present invention, whole blood collected from a subject is fractionated (i.e., separated into components) and only a particular fraction is utilized. In some embodiments only blood serum is used, wherein the serum is separated from the remaining blood sample by isolating the liquid fraction of blood which has been allowed to clot. In some embodiments plasma samples are used, wherein the blood has been pre-treated with an anticoagulant, such as EDTA, sodium citrate (including buffered or non-buffered), heparin, or the like and the supernatant collected and utilized. In some embodiments, the blood is subjected to Ficoll-Hypaque (Pharmacia) gradient centrifugation and the peripheral blood mononuclear cells (PBMC's) are used. Other fractions and/or fractionating techniques known in the art may also be used, for example, blood cells can be sorted using a using a fluorescence activated cell sorter (FACS) e.g. Kamarch, 1987, Methods Enzymol 151:150-165).

5.4 Biomarker and Biomarker Combinations

Table 1 provides a list of proteins which are useful as biomarkers either individually or in combination.

The biomarkers may be used to determine an individual's status with respect to their developing a critical and/or life threatening response to illness. In some cases the biomarkers are individually useful in helping to assess the likelihood of an individual having a critical and/or life threatening response to illness. In some cases the biomarkers are useful in helping to assess whether an individual is at a significantly increased risk of a critical and/or life threatening response. In yet other instances the biomarkers are useful in helping to assess whether an individual is not at a significantly increased risk of having a critical and/or life threatening response. In yet other instances, the biomarkers are useful in determining an appropriate treatment protocol. In yet other instances, the biomarkers are useful in assessing the impact of a treatment protocol on an individual who has a significantly increased risk of a critical and/or life threatening response. In some cases, the biomarkers are useful in determining the likelihood of an individual demonstrating an improvement in their critical and/or life threatening response. The biomarkers are thought to be useful as early indicators of critical and/or life threatening illness because many play roles in endothelial activation and vascular leak, angiogenesis, thrombosis, and inflammation.

TABLE 1

| Protein Name | Symbol/ Alternative Symbols |
|---|---|
| Complement fragment C5a | C5a |
| Angiopoietin-1 | Ang-1 |
| Angiopoietin-2 | Ang-2 |
| 10 kDa interferon gamma-induced protein | IP-10 |
| Soluble intercellular adhesion molecule-1 | sICAM-1 |
| Vascular endothelial growth factor A | VEGF |
| soluble Fms-like tyrosine kinase receptor-1 (also known as soluble VEGFR1 - Vascular Endothelial Growth Factor Receptor 1) | sFlt-1 |
| Chitinase-3-like protein 1 | CHI3L1 |
| Soluble triggering receptor expressed on myeloid cells-1 | sTREM-1 |
| C-reactive protein | CRP |
| Procalcitonin | PCT |
| Angiopoietin-like protein 3 | Ang-like 3; Ang-3 like 1; Ang3L1 |
| Complement factor D | Factor D |
| Interleukin 18 Binding Protein | IL18bp; IL18bpa |
| Endoglin | End; endoglin |
| p-selectin | P-sel; Pselectin; |
| Endothelial soluble Tie-2 Receptor | sTie 2; |
| von Willebrand Factor | vWF |

Combinations of biomarkers of the present invention includes any combination of 2, 3, 4, 5, 6, 7, 8, 9, 10, 11, 12, 13, 14, 15, 16, 17, or all of the biomarkers listed in Table 1 can be used. For instance, the number of possible combinations of a subset m of n proteins in Table 1 above is described in Feller, *Intro to Probability Theory*, Third Edition, volume 1, 1968, ed. J. Wiley, using the general formula:

$$m!/(n)!(m-n)!$$

In one embodiment of the invention, where n is 2 and m is 14, the number of combinations of protein markers selected from Table 1 is:

$$\frac{14!}{2!(14-2)!} = \frac{14x13x12x11x10x9x8x7x6x5x4x3x2x1}{(2x1)(12x11x10x9x8x7x6x5x4x3x2x1)}$$
$$= 91$$

unique two-gene combinations.

In another embodiment of the invention, where n is 2 and m is 18, the number of combinations of protein markers selected from Table 1 is:

$$\frac{18!}{2!(18-2)!} = \frac{18x17x16x15x14x13x12x11x10x9x8x7x6x5x4x3x2x1}{(2x1)(16x15x14x13x12x11x10x9x8x7x6x5x4x3x2x1)}$$
$$= 153$$

The measurement of the gene expression of each of these two-gene combinations, in an additive manner, can be used as described herein. In another embodiment there are 14!/3!(14-3)! or 364 unique three-gene combinations and the measurement of each of these three-gene combinations, in an additive manner, can be used as described herein.

5.5 Biomarker Quantification

Protein biomarkers to be quantified are often first isolated from a sample using techniques which are well known to those of skill in the art. Protein isolation methods can, for example, be such as those described in Harlow and Lane (Harlow, E. and Lane, D., *Antibodies: A Laboratory Manual*, Cold Spring Harbor Laboratory Press, Cold Spring Harbor, N.Y. (1988)).

Detection of quantity or level of the biomarkers in a sample can occur either directly in said sample, or upon further isolation or purification of extracted proteins using one or more techniques known in the art including density gradient centrifugation, ultra-centrifugation, concentration, dialysis, chromatography, precipitation, electrophoresis, flow preparation electrophoresis, selective banding and the like. Commercially available products for purification of proteins from samples, including blood, are also well known in the art including Qiagen®'s AllPrep DNA/RNA/Protein Mini Kit, and Molecular Research Centre's (MRC®) Tri-Reagent® BD-RNA/DNA Protein Isolation Blood Derivative.

Protein biomarkers of a sample can also be differentiated upon purification or partial purification using such standard techniques such as a sodium dodecyl sulfate polyacrylamide gel electrophoresis (SDS-PAGE), potentially in combination with western blotting. Quantities of protein biomarkers can be determined using techniques known in the art. Useful ways to determine such levels include, but are not limited to, Western blots, protein microarrays, and Enzyme-Linked Immunosorbent Assays ("ELISA") and the like. A number of different types of other useful assays that measure the presence of a protein biomarker are well known in the art. Immunoassays may be homogeneous, i.e. performed in a single phase, or heterogeneous, where antigen or antibody is linked to an insoluble solid support upon which the assay is performed. Sandwich or competitive assays may be performed. The reaction steps may be performed simultaneously or sequentially. Threshold assays may be performed, where a predetermined amount of analyte is removed from the sample using a capture reagent before the assay is performed, and only analyte levels of above the specified concentration are detected. Assay formats include, but are not limited to, for example, assays performed in test tubes, wells or on immunochromatographic test strips, as well as dipstick, lateral flow or migratory format immunoassays. Such examples are not intended to limit the potential means for determining the level of a protein biomarker in a sample.

Agents for detecting a protein biomarker may utilize a complementary binding partner capable of binding to a protein of interest. A suitable complementary binding partner can include a nucleic acid aptamer, a peptide aptamer, a peptibody, a mimetic, a polyclonal antibody, a monoclonal antibody or any other protein or nucleic acid, or fragment thereof which is known to have specific interaction with the protein biomarker either in vivo or in vitro, or combinations thereof.

Complementary binding partners, including antibodies, can be conjugated to non-limiting materials such as magnetic compounds, paramagnetic compounds, other proteins such as avidin and/or biotin, nucleic acids, antibody fragments, or combinations thereof and/or can be disposed on an appropriate surfaces to allow detection including glass, polystyrene, polypropylene, polyethylene, dextran, nylon, amylases, natural and modified celluloses, polyacrylamides, gabbros, and magnetite NPV membrane, plastic, including a support intended to be used as a dipstick or a support useful for a microarray.

One or more complementary binding partners used for quantification of the protein biomarker can be operably linked (attached via either covalent or non-covalent methods) to a detectable label. Methods for linking said detectable label to a complementary binding partner is well known in the art (see, e.g., Wong, S. S., Chemistry of Protein Conjugation and Cross-Linking, CRC Press 1991; Burkhart et al., The Chemistry and Application of Amino Crosslinking Agents or Aminoplasts, John Wiley & Sons Inc., New York City, N.Y., 1999).

Useful labels can include, without limitation, fluorophores (e.g., fluorescein (FITC), phycoerythrin, rhodamine), chemical dyes, fluorescent dies or compounds that are radioactive, chemiluminescent, magnetic, paramagnetic, promagnetic, or enzymes that yield a product that may be colored, chemiluminescent, or magnetic. The signal is detectable by any suitable means, including spectroscopic, photochemical, biochemical, immunochemical, electrical, optical or chemical means. In certain cases, the signal is detectable by two or more means.

All protein biomarkers are easily purified from blood, and can be readily used to generate monoclonal and/or polyclonal antibodies using traditional techniques for antibody generation well known in the art. Monoclonal antibodies can be prepared, e.g., using hybridoma methods, such as those described by Kohler and Milstein, Nature, 256:495 (1975) or can be made by recombinant DNA methods (U.S. Pat. No. 4,816,567). See also Goding, Monoclonal Antibodies Principles and Practise, (New York: Academic Press, 1986), pp. 59-103. Kozbor, J. Immunol., 133:3001 (1984); Brodeur et al., Monoclonal Antibody Production Techniques and Applications (Marcel Dekker, Inc.: New York, 1987) pp. 51-63.

Monoclonal and/or polyclonal antibodies that have been used or are known to be available as potentially useful complementary binding partners for detecting the protein biomarkers are disclosed in Table 2 herein.

TABLE 2

| Protein Name | Protein Symbol | Commercially Available Antibody Reference |
| --- | --- | --- |
| Complement fragment C5a | C5a | Abcam® ab11878 |
| Angiopoietin-1 | Ang-1 | Abcam® ab8451 |
| Angiopoietin-2 | Ang-2 | Abcam® ab8452 |
| 10 kDa interferon gamma-induced protein | IP-10 | Abcam® ab8098 |
| Soluble intercellular adhesion molecule-1 | sICAM-1 | R&D Systems® Mab720 |
| Vascular endothelial growth factor A | VEGF | Abcam® Ab46154 |
| Soluble vascular endothelial growth factor receptor 1 | sFlt-1 | R&D Systems® Mab321 |

TABLE 2-continued

| Protein Name | Protein Symbol | Commercially Available Antibody Reference |
|---|---|---|
| Chitinase-3-like protein 1 | CHI3L1 | Abcam ® Ab93034 |
| Soluble triggering receptor expressed on myeloid cells-1 | sTREM-1 | Abcam ® Ab93717 |
| C-reactive protein | CRP | Abcam ® Ab76434 |
| Procalcitonin | PCT | Abcam ® Ab53897 |
| Angiopoietin-like protein 3 | Ang-like 3 | R&D Systems ® MAb38291 |
| Complement factor D | Factor D | R&D Systems ® Mab1824 |
| Interleukin 18 Binding Protein | IL18bpa | Abcam ® Ab52914 |
| Endoglin | END | R&D Systems ® Mab13201 |
| P-Selectin | Psel | Santa Cruz Biotechnology Inc. sc-8419 |
| Endothelial soluble Tie-2 Receptor | sTie 2 | Abcam ® Ab10349 |
| von Willebrand Factor | vWF | Santa Cruz Biotechnology In. sc-365712 |

5.6 Use of Biomarkers and Biomarker Combinations

As taught herein, one or more biomarkers or biomarker combinations can be used to determine the likelihood of a test individual having, or not having a critical and/or life threatening response to illness. In one aspect, the test individual has been diagnosed or differentially diagnosed, prior to use of the biomarkers or biomarker combinations. In another aspect, the test individual has not been diagnosed or differentially diagnosed prior to the use of the biomarkers or biomarker combinations. In other aspects, the test individual has been diagnosed with one or more symptoms indicative of having an illness, but the source or cause of the illness, and/or the appropriate treatment, remains unknown prior to the use of the biomarker or biomarker combinations.

In some embodiments, the biomarker and biomarker combinations determine that the test individual has an increased risk of having a critical and/or life threatening response. In some embodiments, the biomarker and biomarker combinations determine that the test individual has a decreased risk of having a critical and/or life threatening response. In some embodiments, the biomarker and biomarker combinations determine that the test individual has is at a significantly increased risk of having a critical and/or life threatening response. In some embodiments, the biomarker and biomarker combinations determine that the test individual has a significantly decreased risk of having a critical and/or life threatening response. The increased risk or decreased risk is in comparison to a control population. In some embodiments, the control population is a negative control population of individuals not having an increased risk of a critical and/or life threatening response to illness. In some embodiments, the control population is a positive control population of individuals having an increased risk of a critical and/or life threatening response to illness. In some embodiments, the control population is a population of individuals who have had the illness of the test individual and have not developed a critical or life threatening response. In some embodiments the control population is population of normal individuals. In some embodiments, the control population is a population of individuals with the same illness as the test individual. In some embodiments, the control population is a population of individuals who have had the illness and have developed a critical or life threatening response. In some embodiments, the control population is a population of individuals who have not been diagnosed or differentially diagnosed as having any illness which may be critical or life threatening. In some embodiments the population is unbiased with respect to any of the above.

In some embodiments, the biomarker and biomarker combinations can be used to determine that the test individual would benefit from a specific treatment protocol. In some embodiments, the test individual is not diagnosed or differentially diagnosed as having an illness for which a treatment protocol is warranted, but nevertheless the biomarker and/or biomarker combinations can be used to determine that there is an increased likelihood that the test individual would benefit from the application of the treatment protocol. In some embodiments, the test individual is not diagnosed or differentially diagnosed as having an illness for which a treatment protocol is warranted, but nevertheless the biomarker and/or biomarker combinations can be used to determine that there is an increased likelihood that the test individual would not benefit from the application of the treatment protocol. In some embodiments, the control population is a negative control population of individuals who have an illness that would not benefit from the treatment protocol. In some embodiments, the control population is a positive control population of individuals having an illness that would benefit from the treatment protocol. In some embodiments, the control population is a positive control population of individuals with the same illness as the test individual. In some embodiments, the control population is a positive control population of individuals with a different illness as the test individual, but nevertheless having an illness which would benefit from the treatment protocol. In some embodiments, the control population is a negative control population of individuals who have an illness that would not benefit from the treatment protocol.

In order to determine the likelihood of an individual having a critical and/or life threatening response to an illness, the levels of one or more of the protein biomarkers of Table 1 in a sample are detecting and quantified and compared with the quantified control levels of said one or more protein biomarkers in a control population. In order to determine the likelihood of an individual benefiting from the application of a treatment protocol effective for a critical and/or life threatening illness, the levels of one or more of the protein biomarkers of Table 1 in a sample are detecting and quantified and compared with the quantified control levels of said one or more protein biomarkers in a control population.

For each individual protein biomarker, where the level of the protein biomarker in the test individual is significantly different (where by significantly different is meant a statistically significant difference) from the level of the protein biomarker in the control population, it aids in the determination that the test individual is likely to have a different response to a critical and/or life threatening response to illness than the control individual. In some embodiments, the results from a single biomarker may be sufficient to determine that the test individual is at an increased or decreased risk of having a critical and/or life threatening response to illness. Whether a single biomarker is sufficient to determine that the test individual is at an increased or decreased risk of having a critical and/or life threatening response to illness will depend upon the desired sensitivity and/or specificity of the test results. In some embodiments, it will be sufficient that the sensitivity is greater than 51% and the specificity is greater than 51%. In other embodiments, the sensitivity of the test results must be greater than 55%, 60%, 65%, 70%, 75%, 80%, 85%, 90%, 95%, 96%, 97%, 98%, 99% or must be 100%. In some embodiments the specificity of the test results must be greater than 55%, 60%, 65%, 70%, 75%, 80%, 85%, 90%, 95%, 96%, 97%, 98%, 99% or must be 100%.

In some embodiments, in order to achieve the desired sensitivity and/or specificity of the test results, two or more biomarkers, three or more biomarkers, four or more biomarker, five or more biomarkers, six or more biomarkers, seven or more biomarkers, eight or more biomarkers, nine or more biomarkers, ten or more biomarkers, 11 or more biomarkers, 12 or more biomarkers, 13 or more biomarkers, 14 or more biomarkers, 15 or more biomarkers, 16 or more biomarkers, 17 or more biomarkers or all biomarkers must be used in combination.

In some embodiments, each of said two or more biomarkers, three or more biomarkers, four or more biomarker, five or more biomarkers, six or more biomarkers, seven or more biomarkers, eight or more biomarkers, nine or more biomarkers, ten or more biomarkers, 11 or more biomarkers, 12 or more biomarkers, 13 or more biomarkers, 14 or more biomarkers, 15 or more biomarkers, 16 or more biomarkers, 17 or more biomarkers, or all biomarkers are weighted equally to make a determination with respect to the status of a test individual.

In some embodiments, in order to achieve the desired sensitivity and/or specificity, each of said biomarkers in the combination may be weighted differently as determined by a classifier using at least two populations, wherein at least one population has been pre-determined to have a critical and/or life threatening response to an illness, and at least one population has been pre-determined to not have a critical and or life threatening response to an illness.

In some embodiments the classifier is built using logistic regression as the mathematical model. In other embodiments, the classification and/or regression tree analysis is used.

5.7 Kits

The present invention provides kits for measuring the levels of at least 1, at least 2, at least 3, at least 4, at least 5, at least 6, at least 7, at least 8, at least 9, at least 10, at least 11, at least 12, at least 13, at least 14, at least 15, at least 16, at least 17, or any or all combinations of the protein biomarkers of the invention. Such kits comprise materials and reagents required for measuring the levels of such protein biomarkers. As such, the kits provide one or more complementary binding proteins to measure the level of said biomarkers of said combinations. In some embodiments the complementary binding proteins are monoclonal antibodies, and the kit includes antibodies which bind specifically to each of biomarkers to be measured. The kits may additional comprise one or more additional reagents employed in the various methods, such as (1) one or more labelled or non-labelled antibodies which can bind the complementary binding proteins in said kit (e.g. Anti-mouse antibodies (1) labeling reagents ((2) one or more buffer mediums, e.g., hybridization and washing buffers; (3) protein purification reagents; (4) signal generation and detection reagents, e.g., streptavidin-alkaline phosphatase conjugate, chemifluorescent or chemiluminescent substrate, and the like. In particular embodiments, the kits comprise prelabeled quality controlled protein for use as a control.

In some embodiments, an antibody based kit can comprise, for example: (1) at least one first antibody (which may or may not be attached to a support) which binds to a specific protein biomarker; (2) a second, different antibody which binds to either the protein biomarker, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for determining the likelihood an individual is at an increased risk of a critical and/or life threatening response to illness.

5.8 Examples

Example 1 Individual Biomarkers Predictive of Outcome in Pre-Diagnosed Malaria A retrospective case-control study was performed at Mulago Hospital in Kampala studying children with malaria as the illness. Children were enrolled between the ages of 6 months and 12 years old who presenting with clinical signs and symptoms of malaria wherein the diagnosis was confirmed by detecting the presence of *P. falciparum* infections by microscopic analysis were utilized. Children with co-morbidities such as sickle cell trait/disease, HIV co-infection or severe malnutrition were excluded. Using plasma banked samples, various protein biomarkers were isolated and measured in the plasma from the approximately 100 Ugandan children where the diagnosis was confirmed as either cerebral malaria (CM) or severe malarial anemia (SMA) (both illness that can progress to life threatening disease). The levels of each of a selection of specific protein biomarkers was measured in the banked plasma samples and compared as between children who were known to have survived the malaria as compared with the levels of these protein biomarkers in children who died.

Plasma samples were isolated from whole blood after treatment with sodium citrate anticoagulant, and were stored at −20° C. prior to testing. ELISAs were used to quantify the levels of various potential biomarkers including Ang-2, CRP, sTREM-1, IP-10, sFlt-1, sICAM-1, and PCT, in said samples. ELISAs were performed in accordance with manufacturer's instructions with the following changes: assays were performed in a volume of 50 pt/well; plasma samples were incubated overnight at 4° C.; and ELISAs were developed using Extravidin®—Alkaline Phosphatase (Sigma, 1:1000 dilution, 45 min incubation) followed by addition of p-Nitrophenyl phosphate substrate (Sigma) and optical density readings at 405 nm. Assays were developed with tetramethylbenzidine, stopped with $H_2SO_4$, and read at 450 nm. Samples with concentrations below the limit of detection were designated as twice the background level. Background signal was determined from blank wells included on each plate (assay buffer added instead of sample), and background optical density was subtracted from all samples and standards prior to analysis. Samples with optical densities below the lowest detectable standard were assigned the value of that standard.

GraphPad Prism v4, SPSS v18, and MedCalc software were used for analysis. For clinical and demographic variables, differences between groups were assessed using the Chi-square test (categorical variables) or the Kruskal-Wallis test with Dunn's multiple comparison post-hoc tests (continuous variables). The Mann-Whitney U test was used to compare biomarker levels between groups, and p values were corrected for multiple comparisons using Holm's correction.

Levels of protein biomarkers were compared as between children who survived the malaria as compared with children who died from the malaria and are presented as dot plots with medians shown in FIG. 1A. FIG. 1B demonstrates results on the same population for the biomarker sTREM-1, and the dotplot categorizes the individuals has having either survived or died. A Mann Whitney U test was performed for each comparison to determine the statistical significance of the difference as between the two populations of levels, and those biomarkers showing a statistically significant difference between the two populations is shown with a * (p<0.05) or ** (p<0.01) in FIG. 1A, 1B. Within this small sample size, sTie-2 did not reach statistical significance. Nevertheless, given the close interaction between sTie-2 (as the receptor to Ang-2), the fact that Ang-2 did show a statistically significant response, and given the differential trend seen for sTie-2 (despite not reaching statistical significance) we reasonably predict that this biomarker will demonstrate utility when tested with sample populations in greater numbers.

Receiver operating characteristic curves were generated using the non-parametric method of Delong et. al (DeLong E R, DeLong D M, Clarke-Pearson D L (1988) Comparing the areas under two or more correlated receiver operating characteristic curves: a nonparametric approach. Biometrics 44:837-845). Data is shown for biomarkers sICAM-1, sFlt-1, Ang-2, PCT, IP-10, and sTREM-1 in FIG. 2A. As would be understood the area under the ROC curve is indicative of the ability of each biomarker to differentiate between the likelihood of an individual dying and not dying. Shown in dashed reference lines is an ROC curve for a test which has no discriminatory ability. The area under the ROC curve is noted and its statistical significance as either * p<0.05 or ** p<0.01 shown. In parenthesis is the 95% confidence intervals for the area under the curve. FIG. 2B shows the ROC curve for parasitemia, which is currently relied upon to assess the individual's response to malaria. Parasitemia predicts the quantitative content of parasites in the blood and is used as a measurement of parasite load in the organism and an indication of the degree of an active parasitic infection. As can be seen, each of the biomarkers noted is better at predicting death than the currently utilized index of parasitemia.

To evaluate the biomarkers further, the Youden index was used to obtain a cut-point for each biomarker, and clinical performance measures evaluated for these dichotomized biomarkers (Table 3). All parameters presented in Table 3 are presented with 95% confidence intervals shown in brackets. All cut points were determined using the Youden Index (J-max[sensitivy+specificity−1]). For each biomarker is shown the PLR, positive likelihood ratio, NLR the negative likelihood ratio, PPV, the positive predictive value and NPV, the negative predictive value. PPVs and NPVs were based on estimates that 5.7% of CM and SMA diagnosed patients at the Mulago hospital died of the malaria infection. sTREM-1 achieved the highest sensitivity (95.7%) but had low specificity (43.8%), while IP-10 predicted death with the highest overall accuracy (82.6% sensitivity, 85% specificity).

TABLE 3

Clinical Performance of Biomarkers for Predicting Mortality Among Children with Severe Malaria

| | Cut-point | Sensitivity (%) | Specificity (%) | PLR | NLR | PPV (%) | NPV (%) |
|---|---|---|---|---|---|---|---|
| Ang-2 | >5.6 ng/ml | 78.3 (56.3-92.5) | 78.8 (68.2-87.1) | 3.7 (2.9-4.7) | 0.3 (0.1-0.7) | 18.2 (5.8-38.7) | 98.4 (92.4-99.9) |
| sICAM | >645.3 ng/ml | 87.0 (66.4-97.2) | 75.0 (64.1-84.0) | 3.5 (2.8-4.3) | 0.2 (0.06-0.5) | 17.4 (5.9-35.9) | 99.0 (93.2-100) |
| sFlt-1 | >1066.3 pg/ml | 82.6 (61.2-95.0) | 57.5 (45.9-68.5) | 1.9 (1.5-2.5) | 0.3 (0.1-0.8) | 10.5 (3.4-23.1) | 98.2 (90.4-100) |
| PCT | >43.1 ng/ml | 56.5 (34.5-76.8) | 82.5 (72.4-90.1) | 3.2 (2.2-4.7) | 0.5 (0.3-1.0) | 16.3 (3.8-39.5) | 96.9 (90.5-99.5) |
| IP-10 | >831.2 pg/ml | 82.6 (61.2-95.0) | 85.0 (75.3-92.0) | 5.5 (4.5-6.8) | 0.2 (0.07-0.6) | 25 (8.3-49.8) | 98.8 (93.4-100) |
| sTREM-1 | >289.9 pg/ml | 95.7 (78.1-99.9) | 43.8 (32.7-55.3) | 1.7 (1.3-2.2) | 0.1 (0.01-0.7) | 9.3 (3.3-19.6) | 99.4 (90.5-100) |

Example 2 Biomarker Combinations Predictive of Mortality in Pre-Diagnosed Malaria Data was obtained as described in Example 1. The use of biomarker combinations improved the ability to predict the likelihood of an individual's life threatening response in malaria. In this example, a modest number of deaths in the study precluded using multivariable logistic regression analysis to create classifiers with more than 2-3 independent variables (Harrell F E, Jr., Lee K L, Mark D B (1996) Multivariable prognostic models: issues in developing models, evaluating assumptions and adequacy, and measuring and reducing errors. Stat Med 15:361-387). Therefore, as performed in other conditions, (Morrow D A, Braunwald E (2003) Future of biomarkers in acute coronary syndromes: moving toward a multimarker strategy. Circulation 108:250-252; Vinueza C A, Chauhan S P, Barker L, Hendrix N W, Scardo J A (2000) Predicting the success of a trial of labor with a simple scoring system. J Reprod Med 45:332-336), six biomarkers were combined (Ang-2, sICAM-1, sFlt-1, PCT, IP-10 and TREM-1) into a single score. For each marker, one point was assigned if the measured value was greater than the corresponding cut-point, and zero points were assigned if it was lower. A cumulative "biomarker score" was calculated for each patient by summing the points for all six markers. No two dichotomized biomarkers were highly correlated (Spearman's rho <0.6; data not shown), suggesting that each biomarker would contribute unique information to the score since biomarkers which are not correlated indicate that the biomarkers each add new information as compared with single biomarkers alone.

Biomarker score was highly positively correlated with risk of death (data not shown; Spearman's rho=0.96, p=0.003). Scores were elevated among fatalities compared to survivors (median (interquartile range): 5 (4-6) and 1 (0-2.5), respectively, data not shown.

In a univariate logistic regression model, the biomarker score was a significant predictor of death with an odds ratio of 7.9 (95% CI 4.6-54.4) (Table 4, Model 1). After adjustment to exclude parasitemia and age, which have been associated with malaria mortality as predictive factors, the score remained significant with an adjusted odds ratio of 7.8 (4.7-134) (Table 4, Model 2).

ROC curve analysis and cut-point determination were performed as above for various biomarker combinations to determine their utility in as predictive indicators of outcome of illness. Table 5 shows the data resulting from some of the biomarker combinations tested. All combinations demonstrated some utility as predictive indicators of outcome of illness. Additional combinations are shown in Table 6 and Table 6A and 6B. All parameters in the tables are presented with 95% CIs in parentheses. Cut-points were determined using the Youden Index (J=max[sensitivity+specificity−1]).

PLR indicates the positive likelihood ratio; NLR indicates the negative likelihood ratio; PPV is the positive predictive value; and NPV is the negative predictive value.

Using logistic regression on the six biomarker combination of Ang-2, sICAM-1, sFlt-1, PCT, IP-10 and TREM-1, the AUC was 0.96 (0.90-0.99) (data not shown), and a score ≥4 was found to have a 95.7% sensitive and 88.8% specific for predicting death in the samples tested (Table 5, row 1). For logistic regression, linearity of an independent variable with the log odds of the dependent was assessed by including a Box-Tidwell transformation into the model and ensuring that this term was not significant. Bootstrapping (1000 sample draws) was used to generate variance estimates for the cut point. Model goodness-of-fit was assessed by the Hosmer-Lemeshow test and calibration slope analysis (Steyerberg E W, Eijkemans M J, Harrell F E, Jr., Habbema J D (2001) Prognostic modeling with logistic regression analysis: in search of a sensible strategy in small data sets. Med Decis Making 21:45-56). Positive and negative predictive values were calculated using the reported case fatality rate of 5.7% for microscopy-confirmed CM and SMA cases. (Hosmer D W, Lemeshow S. Applied Logistic Regression. 2nd ed. New York: John Wiley & Sons, Inc, 2000). PPVs and NPVs were based on estimates that 5.7% of CM and SMA patients at the Mulago hospital where samples were obtained die of the malaria infection. While the positive predictive value for the six biomarker combination was low (33.9%) given a fatality rate of 5.7%, the negative predictive value (NPV) was 99.7%, indicating that a child with a score ≤3 will likely respond well to standard treatment protocols.

TABLE 4

Association of biomarker score with outcome among children with severe malaria: logistic regression.[a]

|  | Variable | b (95% CI) | SE | Wald | df | p value | OR (95% CI) | Hosmer-Lemeshow test Chi square | df | p value |
|---|---|---|---|---|---|---|---|---|---|---|
| Model 1[b] | Biomarker score | 2.1 (1.5-4.0) | 2.3 | 18.6 | 1 | 0.001 | 7.9 (4.6-54.4) | 3.3 | 5 | 0.66 |
| Model 2[c] | Biomarker score[d] | 2.1 (1.6-4.9) | 21.5 | 18.2 | 1 | 0.001 | 7.8 (4.7-134) | 1.1 | 8 | 1.0 |
|  | Log parasitemia[e] | 0.050 ((−1.1)-1.3) | 2.8 | 0.010 | 1 | 0.91 | 1.1 (0.35-3.6) |  |  |  |
|  | Age | 0.053 ((−0.61)-1.2) | 8.5 | 0.052 | 1 | 0.89 | 1.1 (0.55-3.3) |  |  |  |

[a]The reference category was "survival."
[b]Pseudo-$R^2$ (Cox & Snell) 0.473 and calibration slope 0.98.
[c]Pseudo-$R^2$ (Cox & Snell) 0.474 and calibration slope 1.0.
[d]Biomarker score and log parasitemia had a significant but low correlation (Spearman's rho 0.292, p < 0.01).
[e]Parasitemia was log-transformed in order to achieve linearity with the log-odds of the dependent variable.
SE, standard error;
OR, odds ratio.

TABLE 5

Clinical performance of biomarker combinations for predicting mortality among children with severe malaria.[a]

| Biomarker combination | Number of individuals utilized in generating the data (n). | Threshold (positives based on ROC curves) | Sensitivity (%) | Specificity (%) | PPV | NPV |
|---|---|---|---|---|---|---|
| IP-10, sICAM1 | 104 | 2/2 | 77.3 | 96.6 | 85 | 94.4 |
| IP-10, sICAM1 | 98 (exclude non-CM/SMA fatal) | 2/2 | 93.8 | 96.3 | 83.3 | 98.8 |
| ANG-2, IP10, sICAM1 | 104 | 2/3 | 86.4 | 87.5 | 63.3 | 96.3 |
| ANG-2, IP10, sICAM1 | 98 (exclude non-CM/SMA fatal) | 2/3 | 93.8 | 86.6 | 57.7 | 98.6 |
| ANG-2, IP10, CHI3L1 | 77 | 2/3 | 93.8 | 82.0 | 57.7 | 98.0 |
| ANG-2, IP10, sTREM1 | 77 | 2/3 | 93.8 | 85.2 | 62.5 | 98.1 |
| ANG-2, sICAM1, CHI3L1 | 77 | 2/3 | 93.8 | 93.4 | 78.9 | 98.3 |
| ANG-2, sICAM1, sTREM1 | 77 | 2/3 | 93.8 | 88.5 | 68.2 | 98.2 |
| ANG-2, CHI3L1, sTREM1 | 77 | 2/3 | 81.3 | 85.2 | 59.1 | 94.5 |
| IP10, sICAM1, CHI3L1 | 77 | 2/3 | 93.8 | 88.5 | 68.2 | 98.2 |

TABLE 5-continued

Clinical performance of biomarker combinations for predicting mortality among children with severe malaria.[a]

| Biomarker combination | Number of individuals utilized in generating the data (n). | Threshold (positives based on ROC curves) | Sensitivity (%) | Specificity (%) | PPV | NPV |
|---|---|---|---|---|---|---|
| IP10, sICAM1, sTREM1 | 77 | 2/3 | 93.8 | 86.9 | 65.2 | 98.1 |
| sICAM1, CHI3L1, sTREM1 | 77 | 2/3 | 93.8 | 86.9 | 65.2 | 98.1 |
| ANG-2, IP10, sICAM1, CHI3L1 | 77 | 2/4 | 100.0 | 80.3 | 57.1 | 100.0 |
| ANG-2, IP10, sICAM1, sTREM1 | 77 | 2/4 | 100.0 | 78.7 | 55.2 | 100.0 |
| ANG-2, sICAM1, CHI3L1, sTREM1 | 77 | 2/4 | 100.0 | 82.0 | 59.3 | 100.0 |
| IP10, sICAM1, CHI3L1, sTREM1 | 77 | 2/4 | 100.0 | 77.0 | 53.3 | 100.0 |
| ANG-2, IP10, CHI3L1, sTREM1 | 77 | 2/4 | 100.0 | 73.8 | 50.0 | 100.0 |
| ANG-2, IP10, sICAM1, CHI3L1 | 77 | 3/4 | 87.5 | 93.4 | 77.8 | 96.6 |
| ANG-2, IP10, sICAM1, sTREM1 | 77 | 3/4 | 87.5 | 95.1 | 82.4 | 96.7 |
| ANG-2, sICAM1, CHI3L1, sTREM1 | 77 | 3/4 | 81.3 | 93.4 | 76.5 | 95.0 |
| IP10, sICAM1, CHI3L1, sTREM1 | 77 | 3/4 | 87.5 | 95.1 | 82.4 | 96.7 |
| ANG-2, IP10, CHI3L1, sTREM1 | 77 | 3/4 | 81.3 | 93.4 | 76.5 | 95.0 |
| ANG-2, IP10, sICAM1, CHI3L1, sTREM1 | 77 | 3/5 | 100 | 91.8 | 76.2 | 100 |

TABLE 6

Clinical performance of selected biomarker combinations for predicting mortality among children with severe malaria.[a]

| Combination | Cut-point[b] | Sensitivity (%) | Specificity (%) | PLR[c] | NLR | PPV (%)[d] | NPV (%) |
|---|---|---|---|---|---|---|---|
| (Ang-2, sICAM-1, sFlt-1, PCT, IP-10) | ≥4 | 95.7 (78.1-99.9) | 88.8 (79.7-94.7) | 8.5 (7.6-9.6) | 0.05 (0.007-0.4) | 33.9 (12.8-61.3) | 99.7 (95.2-100) |
| Ang-2, PCT, sICAM-1 | ≥2 | 91.3 (72.0-98.9) | 88.8 (79.7-94.7) | 8.1 (7.0-9.4) | 0.1 (0.02-0.4) | 32.9 (12.1-60.3) | 99.4 (94.7-100) |
| Ang-2, IP-10, PCT | ≥2 | 91.3 (72.0-98.9) | 86.3 (76.7-92.9) | 6.6 (5.7-7.7) | 0.1 (0.02-0.4) | 28.6 (10.2-54.4) | 99.4 (94.6-100) |
| PCT, IP-10, sTREM-1 | ≥2 | 91.3 (72.0-98.9) | 81.3 (71.0-89.1) | 4.9 (4.1-5.7) | 0.1 (0.03-0.4) | 22.7 (8.1-44.8) | 99.4 (94.2-100) |

TABLE 6A

| Biomarker combination | Cut-point | Sens | Spec | PLR | NLR | PPV | NPV |
|---|---|---|---|---|---|---|---|
| Biomarker score (all 6 markers) | ≥4 | 95.7 (78.1-99.9) | 88.8 (79.7-94.7) | 8.5 (7.6-9.6) | 0.049 (0.007-0.4) | 21.9 (4.9-51.3) | 99.8 (95.6-100.0) |
| ANG-2, IP-10, CHI3L1 | ≥2 | 100 (85.2-100) | 81.2 (71.0-89.1) | 5.3 (4.8-5.9) | 0 | 15.0 (3.4-37.2) | 100 (95.5-100) |
| ANG-2, sICAM-1, CHI3L1 | ≥2 | 95.7 (78.1-99.9) | 81.3 (71.0-89.1) | 5.1 (4.4-5.8) | 0.054 (0.007-0.4) | 14.4 (3.1-36.5) | 99.8 (95.2-100) |
| ANG-2, sICAM-1, PCT | ≥2 | 91.3 (72.0-98.9) | 88.8 (79.7-94.7) | 8.1 (7.0-9.4) | 0.098 (0.02-0.4) | 21.2 (4.5-50.5) | 99.7 (95.3-100) |
| ANG-2, IP-10, PCT | ≥2 | 91.3 (72.0-98.9) | 86.3 (76.7-92.9) | 6.6 (5.7-7.7) | 0.10 (0.02-0.4) | 18.0 (3.7-44.8) | 99.7 (95.2-100) |
| sICAM-1, IP-10, CHI3L1 | ≥2 | 91.3 (72.0-98.9) | 83.8 (73.8-91.1) | 5.6 (4.8-6.6) | 0.10 (0.03-0.4) | 15.7 (3.3-39.4) | 99.7 (95.0-100) |
| sICAM-1, PCT, CHI3L1 | ≥2 | 91.3 (72.0-98.9) | 80.0 (69.6-88.1) | 4.6 (3.9-5.4) | 0.11 (0.03-0.4) | 13.1 (2.7-34.3) | 99.6 (94.8-100) |
| sICAM-1, CHI3L1 (alternative dichotomization) | 2 | 91.3 (72.0-98.9) | 85.0 (75.3-92.0) | 6.1 (5.2-7.1) | 0.09 (0.02-0.4) | 16.8 (3.4-42.4) | 99.7 (95.1-100) |

TABLE 6B

| Biomarkers | # +ve BMs | Sen (%) | Spec (%) | NPV |
|---|---|---|---|---|
| sICAM-1, IP-10 | 2/2 | 93.8 | 95.8 | 94 |
| CHI3L1, sTREM-1, sICAM-1 | 2/3 | 93.8 | 84.8 | 98 |
| ANG-2, CHI3L1, sTREM-1, sICAM-1 | 2/4 | 100 | 82.5 | 100 |
| CHI3L1, sTREM-1, ANG-2, IP-10, sICAM-1 | 3/5 | 100 | 87.9 | 100 |

TABLE 6B-continued

| Biomarkers | # +ve BMs | Sen (%) | Spec (%) | NPV |
|---|---|---|---|---|
| CHI3L1, sTREM-1, ANG-2, IP-10, sICAM-1, sFLT-1 | 4/6 | 100 | 90.9 | 100 |

Example 3 Use of Classification Tree Analysis as an Alternative Classifier Predictive of Mortality in Pre-Diagnosed Malaria To explore other synergistic combinatorial strategies, wherein weighting of each biomarker may vary, classification tree analysis was used, which selects and organizes independent variables into a decision tree that optimally predicts the dependent measure. Initially, a model based on IP-10 and sTREM-1 was generated with 43.5% sensitivity and 100% specificity for predicting mortality (FIG. 3). Since in some instances high sensitivity would be of particular importance, the analysis assigning the cost of misclassifying a death as a survivor was weighted as being 10 times greater than the cost of misclassifying a survivor as a death. A model based on IP-10, Ang-2, and sICAM-1 was generated with 100% sensitivity and 92.5% specificity for predicting outcome (cross-validated misclassification rate 15.4%, standard error 4.9%). In summary, combining dichotomized biomarkers using a scoring system or a classification tree predicted severe malaria mortality in our patient population with high accuracy.

Example 4 Individual Biomarkers and Biomarker Combinations Predictive of Patients Developing Toxic Shock Syndrome in Patients with Invasive *S. pyogenes* Disease A prospective, population-based surveillance for invasive group A streptococcal disease was undertaken in Ontario, Canada via mandatory laboratory reporting of *S. pyogenes* isolates from normally sterile sites and thirty-seven patients, enrolled between 1999 and 2009, were included in the study. Informed consent was obtained to collect bacterial isolates and plasma samples, as well as detailed clinical data from interviews with the attending physicians and patient chart review. Patients were considered to have *S. pyogenes* infections which resulted in streptococcal toxic shock syndrome (STSS) (a critical and/or life threatening form of an *S. pyogenes* infection) if they met the current consensus of indicator symptoms including: hypotension in combination with at least two of coagulopathy, acute renal failure, elevated serum aminotransferases, acute respiratory distress syndrome (ARDS), rash, or necrotizing fasciitis. Of the 37 patients, 16 were considered to have invasive streptococcal infection and toxic shock (STSS), while 21 were determined to have invasive streptococcal infection alone (no STSS). The underlying source of the infection was similar between the two groups, with the majority of patients in both groups having skin and soft tissue infections (7 patients (44%) with STSS and 12 patients (57%) with invasive streptococcal infection alone). Presenting group A streptococcal infections in the remaining patients included respiratory tract infections, bacteremia without an identified source, post-partum infection, and peritonitis, and did not differ significantly between the groups. The two groups were significantly different only in the symptomatic diagnostic criteria for STSS; hypotension was present in 100% of patients with STSS and 33% of patients without ($P<0.0001$). Five patients with invasive infection and STSS died as compared to one patient with invasive infection alone (31% versus 5%, $P=0.06$).

Acute phase plasma samples were collected upon study enrollment and stored at minus 70° C. until use. Plasma concentrations of angiopoietins-1 and -2 were measured by ELISA (R&D Systems, Minneapolis Minn.) according to the manufacturer's instructions. The upper and lower limits of detection for the assays were 10,000 pg/mL and 9.77 pg/mL for Ang-1 and 2520 pg/mL and 2.46 pg/mL for Ang-2, respectively. Samples were diluted in assay diluent (1:20 for Ang-1 and 1:4 for Ang-2) to fall within the range of the standard curves.

Angiopoietin dysregulation (a correlated decrease in Ang-1 levels and an increase in Ang-2 levels) was associated with an increased likelihood of the individual having the invasive group A streptococcal disease with STSS as compared with individuals having invasive group A streptococcal disease without STSS (FIG. 4A and FIG. 4B). The median plasma concentration of Ang-1 was lower during the acute phase of illness in patients pre-diagnosed with invasive infection and STSS than in those pre-diagnosed with invasive streptococcal infection alone (13,915 pg/mL vs. 29,084 pg/mL), while the median plasma concentration of Ang-2 was higher (5752 pg/mL vs. 1337 pg/mL). As a result, the normally low Ang-2:Ang-1 ratio was significantly higher amongst patients with invasive infection and STSS as compared to those with invasive streptococcal infection alone (0.437 versus 0.048, $P<0.05$).

Receiver operating characteristic (ROC) curves were generated for Ang-1, Ang-2, and the Ang-2:Ang-1 ratio, and the area under the ROC curves indicated that the degree of magnitude of Ang-1/2 dysregulation accurately differentiated those individuals with STSS from those without STSS (FIG. 4B). Although the ROC curve for plasma Ang-1 concentration did not differ significantly from chance (AUC: 0.683, $P=0.07$), the ROC curves for plasma Ang-2 (AUC: 0.759, $P=0.009$) and for the Ang-2:Ang-1 ratio (AUC: 0.791, $P=0.003$) revealed that both discriminated between patients with STSS and those with invasive streptococcal infection alone (no STSS) and it is anticipated that the ROC curve for plasma Ang-1 would also be discriminatory upon an increased sample size since the ROC curve for plasma Ang-1 concentration trended despite not reaching statistical difference (AUC: 0.683, $P=0.07$).

Example 5 Individual Biomarkers and Biomarker Combinations Predictive of Response in Patients Having Group A Streptococcal Disease Using the samples and methods as outlined in Example 4, we further measured the biomarkers Ang-1, Ang-2 and the ratio of Ang-1/Ang-2 as the patients convalesced to demonstrate the potential for the biomarkers to function as indicators of response to treatment. Ang-1/2 dysregulation was seen to resolve consistent with convalescence in both groups of patients (FIG. 4A). In the cohort of patients with STSS, the median plasma concentration of Ang-1 rose from 13,519 pg/mL to 21,115 pg/mL, the median plasma concentration of Ang-2 decreased fell from 5752 pg/mL to 378 pg/mL ($P<0.01$), and the median Ang-2:Ang-1 ratio fell from 0.437 to 0.019 ($P<0.05$).

Furthermore, in individual patients with STSS, the matched acute and convalescent plasma Ang-2 concentrations and the Ang-2:Ang-1 ratios also differed significantly (FIG. 5) The same pattern was observed in the cohort of patients with invasive streptococcal disease without STSS, the changes in Ang-1/2 concentrations although the changes were more modest. The median plasma concentration of Ang-1 in this group increased from 29,084 pg/mL to 31,743 pg/mL, while the Ang-2 concentration declined from 1337 pg/mL to 535 pg/mL, and the Ang-2:Ang-1 ratio decreased from 0.048 to 0.027.

Example 6 Individual Biomarkers and Biomarker Combinations Predictive of Outcome in Pre-Diagnosed Sepsis A multicenter retrospective analysis was performed on prospectively collected biological and clinical data so as to identify molecular markers demonstrating an increased likelihood of patients dying from severe sepsis. Samples were collected from three tertiary hospital intensive care units (ICU) associated with Hamilton General Hospital in Hamilton, Canada.

Seventy patients with severe sepsis enrolled within 24-hours of admission to the ICU and were followed until day 28, discharge or death. Clinical data and plasma samples were available on admission for all patients and daily for 1 week, then weekly thereafter for 43 of the 70 patients.

Patients were diagnosed as having severe sepsis if they met the modified American College of Chest Physicians/Society of Critical Care Medicine criteria for sepsis known in the art (Bernard G R, Vincent J-L, Laterre P-F, et al. Efficacy and safety of recombinant human activated protein C for severe sepsis. N Engl J Med 2001; 344(10):699-709; Bone R C, Sibbald W J, Sprung C L. The ACCP-SCCM consensus conference on sepsis and organ failure. Chest 1992; 101(6):1481-1483.) Patients were included if they had known or suspected infection as well as at least three of four modified SIRS criteria and at least one of five criteria for organ dysfunction.

Venous blood (4.5 ml) collected from indwelling catheters was transferred into 15 ml polypropylene tubes containing 0.5 ml of 0.105 M buffered trisodium citrate (pH 5.4) and 100 µl of 1 M benzamidine HCl and centrifuged at 1,500 g for 10 min (20° C.). Plasma for analysis was stored in aliquots at −80° C. Commercial enzyme-linked immunoassays (ELISAs) were used to measure levels of biomarkers. Ang-1 and Ang-2 (R&D Systems, Minneapolis, Minn., USA) were measured on available samples from days 1 to 7, 14, and 28. ESEL (R&D Systems, Minneapolis, Minn., USA), sICAM-1 (R&D Systems, Minneapolis, Minn., USA) and vWF (antibody: Dako, Carpinteria, Calif., USA; standard: American Diagnostica, Stamford, Conn., USA), levels were measured on days 1 and 3. All standards, controls and test samples were assayed in duplicate and averaged prior to interpretation. Concentrations were interpolated from four parameter logistic fit curves generated using a standard curve of recombinant human proteins.

It was determined that patients with low Ang-1 plasma levels (≤5.5 ng/mL) at admission were less likely to survive than those with high Ang-1 levels (≥5.6 ng/ml; relative risk 0.49 [95% CI: 0.25-0.98], p=0.046 (FIG. 6A).

Ang-1 levels ≤5.5 ng/mL also remained a significant predictor of mortality at 28 days in a multivariate logistic regression model (adjusted odds ratio 0.282 [95% confidence interval (CI): 0.086-0.93], p=0.037) using known clinical indicators of increased risk of mortality. Age is a known risk factor leading to increased likelihood of death from sepsis. Similarly Multiorgan Dysfunction (MOD) score exists as the current method of measuring and quantifying organ dysfunction, either as a risk factor for death, a measure of severity of illness, or a measure of increased risk for morbidity over time. The multivariate logistic regression model used age (p=0.008) and MOD score (p=0.014) as additional clinical biomarkers, suggesting that Ang-1 provides independent prognostic information above and beyond age and MOD scores alone.

This finding is supported by receiver operating characteristic (ROC) curve analysis (FIG. 6B) illustrating the apparent added sensitivity and specificity in predicting 28-day mortality when comparing plasma Ang-1 levels (area under the ROC curve (AUROC): 0.62 [95% CI: 0.50-0.76]), MOD score (AUROC: 0.64 [95% CI: 0.51-0.77]) or age (AUROC: 0.68 [95% CI: 0.55-0.80]) with the combination of the three variables (AUROC: 0.79 [95% CI: 0.67-0.90]).

Example 7 Individual Biomarkers and Biomarker Combinations as Early Predictors of Risk of Mortality in Patients with Sepsis As noted, the current standard for determining an individuals increased likelihood of death from sepsis is the Multiorgan Dysfunction (MOD) score. Using samples and methods as described in Example 6, the level of Ang-2 was measured and correlated with the MOD score across the population of individuals tested. As noted in FIG. 7A, the level of Ang-2 correlated (as noted on the y axes in ng/ml) when compared with the MOD score (as noted on the x axis) as a predictor of mortality, with a statistical significance of p<0.0001 as tested using as a single biomarker was demonstrated. The ability of the Ang-2 levels to act as an earlier predictor of mortality was analyzed by similarly comparing the level of Ang-2 (ng/ml) taken from patients one day prior to the evaluation of the patient as determined by MOD score. As can be seen in FIG. 7B, Ang-2 levels measured on day x predicted the clinical condition on the next hospital day (i.e. day x+1). There was a strong statistical correlation (P<0.0001) between the Ang-2 levels performed on day x compared to the MOD score on the next hospital day (day x+1), indicating Ang-2 is an earlier indicator of disease progression and risk of mortality than the current standard of the MOD score.

Example 8 Individual Biomarkers and Biomarker Combinations Predictive of Patients of Having Hemolytic Uremic Syndrome as a Result of an *E. Coli* Infection A population-based surveillance study for *E. coli* O157: H7 infection in children less than 10 years of age was undertaken in Washington, Oregon, Idaho, and Wyoming through mandatory laboratory reporting of positive stool cultures. Seventy-eight children, enrolled between 1998 and 2005, from whom a positive stool culture was obtained within the first 7 days of illness were included for this analysis. Phlebotomy was conducted at enrollment and as clinically indicated thereafter. HUS was diagnosed as hemolytic anemia (a hematocrit <30% with evidence of schistocytes on peripheral blood film), thrombocytopenia (platelet count <150 000/mm3), and renal insufficiency (serum creatinine above the age-adjusted upper limit of normal); participants who had not met these criteria by day 14 of illness were considered to have had uncomplicated infection.

84 serum samples were tested: 26 from patients on the day of diagnosis of HUS, 8 from patients who would subsequently be diagnosed with HUS but had not yet met diagnostic criteria (pre-HUS), and 50 from patients with uncomplicated infection. Six patients had samples taken both prior to (pre-HUS) and on the day of HUS diagnosis.

Serum samples were stored in aliquots at −80° C. until use. To measure angiopoietin levels in cell culture supernatant, HMVEC were grown to confluence in complete medium in 6-well plates. Complete medium was replaced with basal medium lacking serum and growth factors on the day of toxin treatment. Shiga toxin or vehicle was added 4 hours later, and aliquots of medium were taken at 24 hours following toxin addition, centrifuged to remove dead cells, and likewise stored at −80° C. until use.

Serum and supernatant concentrations of Ang-1 and Ang-2 were measured by ELISA (R&D® Systems, Minneapolis Minn.) as per the manufacturer's instructions. The technical upper limits of detection were 10,000 pg/mL for Ang-1 and 2520 pg/mL for Ang-2, yielding effective upper limits of detection of 200,000 pg/mL and 10,080 pg/mL, respectively, for the dilutions employed in the assay. Lower limits of detection for the assay were 9.77 pg/mL for Ang-1 and 2.46 pg/mL for Ang-2.

Angiopoietin dysregulation (decreased Ang-1 and increased Ang-2) was found to be associated with illness severity. The median serum Ang-1 concentration in patients with uncomplicated infection was significantly higher than in those patients with HUS (77, 357 pg/mL [interquartile range (IQR): 53, 437-114, 889 pg/mL] versus 10, 622 pg/mL [IQR: 3464-43, 523 pg/mL]), P<0.001 (FIG. 8A). Conversely, the median serum Ang-2 concentration was significantly lower in those with uncomplicated infection than in those with HUS (1140 pg/mL [IQR: 845-1492 pg/mL] versus 1959 pg/mL [IQR: 1057-2855 pg/mL]), P<0.05. Finally, the Ang-2:Ang-1 ratio was 0.014 (IQR: 0.011-0.023) in patients with uncomplicated infection, and more than 10-fold higher, at 0.18 (IQR).

In addition, the serum Ang-1 concentration at the time of presentation to hospital effectively discriminated between two populations of clinically indistinguishable children: 1) those with uncomplicated hemorrhagic colitis and 2) those with hemorrhagic colitis who would eventually develop HUS (Area under the Receiver operating characteristic (ROC) curve [AUC]: 0.785, 95% confidence interval (CI): 0.641-0.923; P=0.01) (FIG. 8B).

The serum Ang-1 and Ang-2 concentrations reported here for children with uncomplicated infection are comparable to those found in the serum of healthy children and adults, and are in keeping with the clinical observation that there is little if any endothelial activation present in these patients. In contrast, the relative deficit of Ang-1 and excess of Ang-2 found in children with HUS is in keeping with what is anticipated to be significant endothelial cell activation in these patients.

Example 9 Individual Biomarker of Outcome in Pre-Diagnosed Malaria and Use in Conjunction with Other Clinical Indicators of Outcome A retrospective case-control study was performed for children presenting with fever to the Queen Elizabeth Centre Hospital in Blantyre, Malawi. Children were between 6 months and 14 years of age and recruited between the years 1997 and 2009. EDTA Plasma samples were obtained subsequent to obtaining informed consent. Children were characterized based on their status with respect to Cerebral malaria (CM) and also based on retinal indicators such as hemorrhages, retinal whitening, or vessel abnormalities. EDTA Proteins isolated from Plasma samples were subject to ELISAs to quantify the levels of various potential biomarkers including Ang-2, Ang-1, and sTie-2.

Comparisons of continuous variables were performed using the Mann-Whitney U test and Spearman rank correlation coefficient. Comparisons of proportions were performed using the Person chi-square test, linear by linear association, or Fisher's exact test. Odds rations (ORs were calculated using Pearson chi-square or logistic regression models to adjust for covariates. Bonferroni adjustmens were used to account for multiple comparisons.

Logistic regression and CRT analysis was used to generate prognostic models using routine clinical parameters in combination with the protein biomarkers. A clinically predictive model of mortality was generated using solely the clinical parameters readily available (Age, BCS, respiratory distress, severe anemia), and probabilities from this clinical model were used to generate a c-index (equivalent to the area under the receiver operating characteristic curves) of 0.73 (95% confidence interval [CI], 0.65-0.79) (data not shown).

Using these clinical model as a foundation, biomarker tests, either individually or in combination, were added to determine whether the biomarkers would significantly improve the predictive accuracy of the clinical parameters model alone. When the clinical model was combined with all three biomarkers Ang-1, Ang-2 and sTie-2, the resulting model had a c-index of 0.79 (95% confidence interval [CI], 0.72-0.84) which was significantly better than the clinical model alone (p=0.03) (data not shown).

Example 10 Diagnosis of a Test Individual Using Biomarker Combination Predictive of a Critical and/or a Life Threatening Response Classifiers of the invention are generated using the detected levels of protein biomarkers Ang-1, Ang-2, IP10 and CHI3L1 in a population of individuals who demonstrate a critical and/or life threatening response to illness as compared with the detected levels of protein biomarkers Ang-2, IP10 and CHI3L1 in a control population of individuals who are normal. Logistic regression is applied to differentiate the two populations and generates an equation which has a sensitivity of 90% and a specificity of 95%.

Levels of protein biomarkers Ang-2, IP10 and CHI3L1 are determined using a standard ELISA test on a serum sample from a test individual who may potentially have been exposed to an *E. coli* infection, but has not yet been diagnosed with an *E. coli* infection. In accordance with the logistic regression equation generated from the classifier as described, the test individual is classified as either having or not having a critical and or life threatening response to illness.

Example 11 Determining the Likelihood of a Test Individual Having a Critical and/or Life Threatening Response to Disease Using Biomarker Combination Predictive of a Critical and/or a Life Threatening Response Despite the Test Individual not being Diagnosed or Differentially Diagnosed Protein levels of the biomarkers noted in Table 1 are detected in whole blood samples from a population of individuals, wherein the individuals have a critical illness selected from the list of malaria, toxic shock syndrome, Group A streptococcal disease, sepsis, and an *E. Coli* infection, but where the individuals do not develop a critical or life threatening response to the critical illness. Protein levels of the biomarkers noted in Table 1 are also detected in whole blood samples from a second population of individuals, where the individuals do develop a critical response to an illness which is selected from the list of malaria, toxic shock syndrome, Group A streptococcal disease, and an *E. Coli* infection. Classifiers are generated using the data generated from the two populations, in particular ELISA testing is done on the whole blood samples for each individual of each population using the antibodies noted in Table 2, and logistic regression is applied to differentiate the two populations. For each equation generated, wherein the area under the curve indicates a sensitivity of greater than 90% and a sensitivity greater than 90%, the classifier is utilized to determine the likelihood that a test individual suspected of having malaria is likely to have a critical or life threatening response and should be treated as if the individual has severe malaria. Those individuals identified are treated intravenously with drugs and fluids in accordance with the gold standard treatment for severe malaria as dictated by North American hospitals.

Example 12 Determining the Likelihood of a Test Individual Having a Critical and/or Life Threatening Response to Disease Using Predictive Biomarker Combinations with a Test Individual Suspected of Having Malaria A serum sample is taken from a test individual suspected of having been exposed to malaria, and displaying flu like symptoms. ELISA testing is done on the serum sample using each of the antibodies noted in Table 2. The results of the ELISA testing are used in conjunction with the biomarker combinations noted in Table 5 and Table 6, and for each biomarker combination, a biomarker score was determined as done in Example 2 using a one point for each biomarker of the biomarker combination, wherein the point was assigned if the measured value was greater than the corresponding cut-point as determined in Example 2. The results of each biomarker combination being indicative (with varying degrees of sensitivity and specificity) whether the test individual has an increased likelihood of having severe malaria and should be treated accordingly.

Example 13 Determining the Likelihood of a Test Individual Having a Critical and/or Life Threatening Response to Disease Using a Test Individual Suspected of Having Pneumonia A serum sample is taken from a test individual suspected of having pneumonia. ELISA testing is done on the serum sample using each of the antibodies noted in Table 2 and determining a level of protein selectively hybridizing to the antibody in the serum sample. The resulting data is used in conjunction with the biomarker combinations noted in Example 4, and the levels of protein in the test sample compared to the levels of protein for each biomarker of the biomarker combinations in a population of individuals who have been determined to have pneumonia and have not developed a life threatening response, and a population of individuals who have been determined to have pneumonia and have developed a life threatening response. The biomarker level of said test individual is compared with said biomarker level in the two control populations for each biomarker of the combination, and the combined result is analyzed to determine whether the test individual is more akin to the control population having pneumonia and not developing a life threatening response and the control population having been diagnosed as having pneumonia and developing a life threatening response, wherein the results being more akin to the control population having pneumonia and developing a life threatening response is indicative of the test individual having an increased likelihood of having or developing a life threatening response to pneumonia.

Example 14 Determining the Likelihood of a Test Individual Having a Critical and/or Life Threatening Response to Disease Using a Test Individual Suspected of Having an *E. Coli* Infection A whole blood sample is taken from a test individual suspected of having an *E. Coli* infection as a result of exposure to a tainted water supply. As a result of inadequate testing facilities, the test individual is not diagnosed for Hemolytic Uremic Syndrome, and is not tested to confirm an *E. coli* infection. ELISA testing is done on the serum sample using the antibodies noted in Table 2 and determining a level of each protein in the sample corresponding to the biomarkers noted in Table 1. Protein levels of the biomarkers noted in Table 1 are utilized with classifiers generated from comparing the levels of said biomarkers as determined from two separate populations, a population of individuals who have *E. coli* infections, but do not develop Hemolytic Uremic Syndrome, and a population of individuals who have *E. coli* infections and have Hemolytic Uremic Syndrome. Classifiers are chosen which have a sensitivity of greater than 90% and a sensitivity greater than 90%. The test individual is subsequently treated for Hemolytic Uremic Syndrome if results of the classifiers indicate the sample is sufficiently akin to the population of individuals developing Hemolytic Uremic Syndrome.

Example 15 Determining the Likelihood of a Test Individual Having Pneumonia Using Agnostic Biomarkers, Individually, and in Combination, as Shown by the Ability to Differentiate Children Presenting with Cough and Fever Who have Pneumonia (CXR+) as Compared with Children Having Clinical Pneumonia Using WHO Standards A prospective study was done with Children presenting to a community health facility in Africa with fever and upper respiratory tract symptoms. ELISA testing was done on the serum samples from these children using antibodies against the following panel of nine biomarkers selected from Table 1: CRP, PCT, sTie-2, Endoglin, P-selectin, vWF, CHI3L1, IL18bpa, and Angiopoietin—like protein 3. The nine biomarkers individually, and in combinations, were tested for their ability to differentiate between children later diagnosed as having pneumonia using the north American gold standard of a chest x-ray (CXR+Pneumonia) (n=30) or children later diagnosed as having pneumonia by applying WHO Standards of clinical pneumonia, but did not show pneumonia by chest x-ray (CXR−Pneumonia n=90). WHO Standards for determining pneumonia rely on a determination of Tachypnea as determined by measuring respiratory rates taking into account the age of the child as follows: a respiratory rate >60 breaths/minute in children <2 months of age, >50 breaths/minute in children 2 to 12 months of age, and >40 breaths/minute in children ≥1 year of age. Children who were neither CXR+ Pneumonia or CXR− Pneumonia were classified as having an upper respiratory infection which was not pneumonia (URTI) (n=90).

Demographic and clinical characteristics of all children who presented with fever and upper respiratory tract symptoms are shown in Table 7.

TABLE 7

Demographic/clinical characteristics of CXR+ pneumonia, CXR− pneumonia

|  | CXR+ pneumonia n = 30 | Clinical pneumonia (CXR−) n = 90 |
|---|---|---|
| Age (months) | 19.4 (3.6, 100.0) | 14.6 (2.3, 112.8) |
| Gender (% male) | 36.7% | 61.1% |
| Study site (% Dar es Salaam) | 46.7% | 36.7% |
| Temperature (° C.) | 38.7 (38.0, 40.5) | 38.4 (38.0, 40.4) |
| Days of fever prior to presentation | 2.5 (1-5) | 3 (1-6) |
| Respiratory rate (/min) | 53 (32-90) | 50 (40-70) |
| Heart rate (/min) | 129.5 (84-169) | 124 (91-180) |
| Severe (%) + | 30.0% | 23.3% |
| Hemoglobin (g/dL) | 9.4 (5.5, 17.9) | 9.7 (3.8, 13.6) |

TABLE 7-continued

Demographic/clinical characteristics of CXR+ pneumonia, CXR− pneumonia

|  | CXR+ pneumonia n = 30 | Clinical pneumonia (CXR−) n = 90 |
|---|---|---|
| Leukocyte count ($\times 10^9$/mL) | 23.6 (7.4, 38.7) | 11.7 (3.5, 49.9) *** |
| Neutrophil count (units) | 63.4 (35.0, 87.9) | 49.8 (8.7, 83.2) ** |

Continuous variables are represented as: Median (range)
+ indicates symptoms considered "severe" in accordance with WHO Integrated management of childhood Illness (IMCI) standards.

Each biomarker was individually tested for its ability to discriminate between CXR+ pneumonia (pneumonia confirmed by chest x-ray), and CXR− clinical pneumonia (classified as pneumonia according to WHO standards, but negative for pneumonia as determined by chest x-ray). The results of the bivariate analysis are shown in Table 8.

| | | CXR+ vs. Clinical pneumonia | |
|---|---|---|---|
| Biomarkor& | n | Odds Ratio (CI) | p-value* |
| Ang-L-3 (ng/mL, log) | 120 | 1.01 (0.39, 2.60) | 0.984 |
| CHI3L1 (ng/mL, log) | 120 | 3.30 (1.87, 5.83) | <0.001* |
| CRP (μg/mL, log) | 120 | 3.20 (2.01, 5.11) | <0.001* |
| sEndoglin (ng/mL) | 120 | 0.91 (0.79, 1.05) | 0.186 |
| IL-18 BP (ng/mL, log) | 120 | 1.23 (0.62, 2.44) | 0.546 |
| PCT (ng/mL, log) | 120 | 1.80 (1.27, 2.55) | 0.001* |
| pSelectin (ng/mL, log) | 120 | 1.39 (0.94, 2.04) | 0.006 |
| sTie-2 (ng/mL) | 120 | 0.87 (0.32, 2.35) | 0.784 |
| vWF (ug/mL) | 120 | 1.38 (0.82, 2.32) | 0.231 |
| Age (log month) | 120 | 1.86 (1.06, 3.24) | 0.038 |
| Temperature | 120 | 1.05 (0.99, 1.12) | 0.125 |
| Heart rate | 120 | 1.00 (0.99, 1.02) | 0.602 |
| Respiratory rate | 120 | 1.01 (0.96, 1.06) | 0.742 |
| Site (Dar Es Salaam vs. Ifakara) | 120 | 1.33 (0.65, 3.48) | 0.333 |
| WBC | 119 | 7.35 (2.74, 19.73) | <0.001* |
| Male | 120 | 0.37 (0.16, 0.87) | 0.022* |

&Treated as continuous and tested using logistic regression. For all biomarkers except sEndoglin, log transformed variables were used.
* P-values in bold represent statistically significant markers (p < 0.05). After accounting for multiple comparisons of hypothesized biomarkers, p-value ≤ 0.0056 (0.05/9) marked with *.
Analyzed age, temperature, fever duration, heart rate, respiratory rate, hemoglobin, WBC, ALT, sex, site, convulsions, dehydration, jaundice, palm pallor, chest indrawing, nose flapping, grunting, chest auscultation, wheezing, date, HIV status.

Individually, biomarkers CRP, PCT, CHI3L1 and P-selectin were found both by univariate analysis, and by Mann Whitney (data not shown) to differentiate between the two groups of children. Table 9 shows the diagnostic cut-off points of each of CRP, PCT, CHI3L1 and P-selectin as determined by the Receiver Operator Curves (ROC Curves), and the sensitivity and specificity of the individual biomarkers. Sensitivity (Sens) and Specifity (Spec) of the combination, along with the positive likelihood ratio (PLR), negative likelihood ration (NLR) positive predictive value (PPV) and negative predictive value (NPV) are shown.

TABLE 9

|  | AUC* | Cutpoint** | Sens | Spec | PLR | NLR | PPV | NPV |
|---|---|---|---|---|---|---|---|---|
| CHI3L1 | 0.80 | >57.0 ng/mL | 93.3 | 64.4 | 2.6 | 0.10 | 39.6 | 97.5 |
| CRP | 0.86 | >45.9 ug/mL | 80.0 | 81.1 | 4.2 | 0.25 | 51.4 | 94.2 |
| PCT | 0.71 | >0.51 ng/mL | 70.0 | 70.0 | 2.3 | 0.43 | 36.8 | 90.3 |
| Pselectin | 0.62 | >59.0 ng/mL | 70.0 | 62.2 | 1.9 | 0.48 | 31.7 | 89.2 |

*AUC = area under the ROC curve
**Cut-points based on Youden index: J = max{sens + spec − 1}

Additionally classification and regression tree analysis (CRT) was performed to demonstrate the utility of the biomarker combinations of the tested nine biomarkers. While it is anticipated that numerous combinations and variations have utility, various criteria were set including the number of biomarkers from which to select the optimum combination, whether to select a specific cut-off point for any given biomarker (e.g. dichotomize) or to allow a continuous range; the minimum number of nodes and maximum levels per tree to avoid overfitting, and the ability to set misclassification costs to preferentially avoid e.g. false so as to select preferential biomarker combinations. Table 10 and Table 11 show various examples of combination models chosen on the basis of varied input, and show the Sensitivity (Sens) and Specifity (Spec) of the combination, along with the positive likelihood ratio (PLR), negative likelihood ration (NLR) positive predictive value (PPV) and negative predictive value (NPV). Similarly, FIG. 9 demonstrates the CRT analysis of the combination of Model 1 in Table 10 in a tree format wherein the combinatorial power added by each biomarker in differentiating between the two populations (CXR+ pneumonia as compared to Clin pneumonia (or CXR− pneumonia) is shown.

TABLE 10

| | Biomarker entered | Other | Markers | Sens | Spec | PLR | NLR | PPV | NPV |
|---|---|---|---|---|---|---|---|---|---|
| 1 | All 9, continuous variables | Nodes: 10 parent, 5 child 3x misclassification cost** | CRP, Endoglin, Pselectin | 93.3 | 76.7 | 4.0 | 0.1 | 50.0 | 97.9 |
| 2 | All 9 continuous variables | Nodes: 10 parent, 5 child 3x misclassif. Cost Tree limited to 2 levels*** | CRP, Endoglin | 86.7 | 81.1 | 4.6 | 0.2 | 53.4 | 96.1 |
| 3 | All 9, continuous variables | Nodes: 10 parent, 5 child\| 5x misclassif. Cost\| Tree pruned | CHI3L1, CRP | 93.3 | 74.4 | 3.6 | 0.1 | 47.7 | 97.8 |
| 4 | All 9, continuous except dichotomized CRP, PCT* | Nodes: 10 parent, 5 child\| 2x misclassif. Cost Tree limited to 2 levels | CRP, CHI3L1, Endoglin | 90.0 | 81.1 | 4.8 | 0.1 | 54.3 | 97.0 |
| 5 | All 9; continuous except dichotomized CRP, PCT* | Nodes: 10 parent, 5 child 2x misclassif. Cost Tree pruned | CRP, CHI3L1 | 80.0 | 85.6 | 5.6 | 0.2 | 58.1 | 94.5 |

*Dichotomized CRP (40 ug/mL) and PCT (0.5 ng/mL) because POC tests already exist at these cut-offs
**Misclassification costs always in favour of increased sensitivity for CXR+ pneumonia
***Truncated Model 1 after 2 splits

TABLE 11

| Model | Biomarkers entered | Model Parameters | Selected Markers | Sens | Spec | PPV | NPV |
|---|---|---|---|---|---|---|---|
| 1 | Chi3L1, CRP | Nodes: 10 parent, 5 child 1x misclassification cost[1] | Chi3L1, CRP | 70.1 | 91.1 | 72.4 | 90.1 |
| 2 | Chi3L1, PCT | Nodes: 10 parent, 5 child 1x misclass. cost | Chi3L1, PCT | 53.3 | 93.3 | 72.7 | 85.7 |
| 3 | Chi3L1, Tie-2 | Nodes: 10 parent, 5 child 1x misclass. cost | Chi3L1, Tie-2 | 40.0 | 97.8 | 85.7 | 83.0 |
| 4 | Chi3L1, vWF | Nodes: 10 parent, 5 child 1x misclass. cost | Chi3L1, vWF | 73.3 | 84.4 | 61.1 | 90.5 |
| 5-7 | a. Chi3L1, Pselectin b. Chi3L1, Endoglin c. Chi3L1, IL 18bpa | Nodes: 10 parent, 5 child 1x misclass. cost | Chi3L1[2] | 53.3 | 98.9 | 87.5 | 79.5 |
| 8 | Chi3L1, CRP, PCT | Nodes: 10 parent, 5 child 1x misclass. cost | CRP | 70.0 | 91.1 | 72.4 | 90.1 |
| 9 | Chi3L1, CRP, Pselectin | Nodes: 10 parent, 5 child 1x misclass. cost | Chi3L1, CRP | 56.7 | 96.7 | 85.0 | 87.0 |
| 10 | Chi3L1, PCT, Pselectin, Endoglin | Nodes: 10 parent, 5 child 1x misclass. cost | Chi3L1, PCT | 53.3 | 93.3 | 72.7 | 85.7 |

TABLE 11-continued

| Model | Biomarkers entered | Model Parameters | Selected Markers | Sens | Spec | PPV | NPV |
|---|---|---|---|---|---|---|---|
| 11 | All markers[3] | Nodes: 10 parent, 5 child 1x misclass. Cost Tree pruned | CRP, Tie2, Ang3L1 | 70.0 | 91.1 | 72.4 | 90.1 |
| 12 | All markers[3] | Nodes: 10 parent, 5 child 3x misclass. cost | CRP, Endoglin, Pselectin | 93.3 | 76.7 | 50.0 | 97.9 |
| 13 | All markers[3] | Nodes: 10 parent, 5 child 3x misclass. Cost Tree limited to 2 levels[4] | CRP, Endoglin | 86.7 | 81.1 | 53.4 | 96.1 |
| 14 | All markers[3] | Nodes: 10 parent, 5 child 5x misclass. cost Tree pruned | CHI3L1, CRP | 93.3 | 74.4 | 47.7 | 97.8 |
| 15 | All 9, continuous except dichotomized CRP, PCT[5] | Nodes: 10 parent, 5 child 2x misclassif. cost Tree limited to 2 levels | CRP, CHI3L1, Endoglin | 90.0 | 81.1 | 54.3 | 97.0 |
| 16 | All 9; continuous except dichotomized CRP, PCT[5] | Nodes: 10 parent, 5 child 2x misclassif. cost Tree pruned | CRP, CHI3L1 | 80.0 | 85.6 | 58.1 | 94.5 |

[1]Misclassification costs always in favour of increased sensitivity for CXR+ pneumonia
[2]Other biomarkers not selected in model.
[3]All markers: Chi3L1, CRP, PCT, Endoglin, P-selectin, vWVF, Ang3L1, Tie-2, IL18bpa
[4]Truncated Model 1 after 2 splits
[5]Dichotomized CRP (40 ug/mL) and PCT (0.5 ng/mL) because POC tests already exist at these cut-offs Example 16 Determining the Likelihood of a Test Individual Having Pneumonia Using Agnostic Biomarkers, Individually, and in Combination, as Shown by the Ability to Differentiate Children Presenting with Cough and Fever Who have Pneumonia (CXR+) as Compared with Children Having Other Upper Respiratory Infections (URI)

As described in Example 15, a prospective study was done with Children presenting to a community health facility in Africa with fever and upper respiratory tract symptoms. ELISA testing was done on the serum samples from these children using antibodies against the following panel of nine biomarkers selected from Table 1: CRP, PCT, sTie-2, Endoglin, P-selectin, vWF, CHI3L1, IL18bpa, and Ang3L1. The nine biomarkers individually, and in combinations, were tested for their ability to differentiate between children later diagnosed as having pneumonia using the north American gold standard of a chest x-ray (CXR+Pneumonia) (n=30) or age, sex, clinical site and date matched children having upper respiratory infections not confirmed as pneumonia (n=90). Single parameter biomarkers were evaluated and compared for ability to differentiate between (a) CXR+ pneumonia vs. CXR–clinical pneumonia and (b) CXR+ pneumonia vs. other upper respiratory tract infections (URTI) with the exclusion of bronchiolitis (ARIs). Results are shown in Table 12.

TABLE 12

| | Biomarker[&] | | | | | |
|---|---|---|---|---|---|---|
| | CXR+ vs. Clinical pneumonia | | | CXR+ vs. Other ARIs[$] | | |
| | n | Odds Ratio (CI) | p-value* | n | Odds Ratio (CI) | p-value* |
| Ang-Like-3 (ng/mL) | 120 | 1.01 (0.39, 2.60) | 0.984 | 120 | 1.27 (0.48, 3.4) | 0.63 |
| CHI3L1 (ng/mL) | 120 | 3.30 (1.87, 5.83) | <0.001* | 120 | 4.39 (2.10, 9.18) | <0.001* |
| CRP (µg/mL) | 120 | 3.20 (2.01, 5.11) | <0.001* | 120 | 3.36 (1.88, 6.00) | <0.001* |
| sEndoglin (ng/mL) | 120 | 0.91 (0.79, 1.05) | 0.186 | 120 | 0.99 (0.89, 1.10) | 0.803 |
| IL-18 bp (ng/mL) | 120 | 1.23 (0.62, 2.44) | 0.546 | 120 | 1.54 (0.77, 3.05) | 0.221 |
| PCT (ng/mL) | 120 | 1.80 (1.27, 2.55) | 0.001* | 120 | 1.93 (1.28, 2.91) | 0.002* |
| p-Selectin (ng/mL) | 120 | 1.39 (0.94, 2.04) | 0.006 | 120 | 1.51 (0.97, 2.35) | 0.067 |
| sTie-2 (ng/mL) | 120 | 0.87 (0.32, 2.35) | 0.784 | 120 | 3.01 (1.00, 9.01) | 0.049 |
| vWF (ug/mL) | 120 | 1.38 (0.82, 2.32) | 0.231 | 120 | 1.43 (0.83, 2.45) | 0.196 |
| Age_log[#] | 120 | 1.86 (1.06, 3.24) | 0.030 | 120 | 1.54 (0.52, 4.52) (matching variable) | 0.436 |

TABLE 12-continued

| | Biomarker[&] | | | | | |
|---|---|---|---|---|---|---|
| | CXR+ vs. Clinical pneumonia | | | CXR+ vs. Other ARIs[$] | | |
| | n | Odds Ratio (CI) | p-value[%] | n | Odds Ratio (CI) | p-value[%] |
| Temperature | 120 | 1.05 (0.99, 1.12) | 0.125 | | n/a | |
| Heart rate | 120 | 1.00 (0.99, 1.02) | 0.602 | 120 | 1.35 (1.16, 1.57) | <0.001* |
| Respiratory rate | 120 | 1.01 (0.96, 1.06) | 0.742 | 120 | 1.05 (1.03, 1.08) | <0.001* |
| WBC | 119 | 7.35 (2.74, 19.73) | <0.001* | 119 | 8.45 (2.91, 24.55) | <0.001* |
| Male | 120 | 0.37 (0.16, 0.87) | 0.022* | 120 | n/a (matched on sex) | |

[&] Treated as continuous. For all markers except sEndoglin, log transformed variables were used.
Patients in CXR+ vs CXR− analysis were an unmatched and logistic regression was used. For CXR+ vs. URTI analysis, conditional logistic regression was used because patients were matched on age, sex, site and date.
[$] Excludes bronchiolitis
[%] P-values in bold represent statistically significant markers (p < 0.05). After accounting for multiple comparisons, p-value ≤0.0056 (0.05/9) marked as *.
[#] Analyzed age, temperature, fever duration, heart rate, respiratory rate, hemoglobin, WBC, ALT, sex, site convulsions, dehydration, jaundice, palm pallor, chest indrawing, nose flapping, Similar individual biomarkers were able to differentiate CXR+ pneumonia as compared with other upper respiratory tract infections including biomarkers CRP, PCT, and CHI3L1. P-selectin was also identified as a statistically significant individual biomarker when analyzed by Mann Whitney (p=0.044) (data not shown), but not when analyzed utilizing Kruksill Wallis analysis with Dunn's post tests (data not shown). In all cases URTI and CXR− clinical pneumonia were indistinguishable using individual biomarkers (data not shown). Table 13 shows the diagnostic cut-off points of each of CRP, PCT, CHI3L1 and P-selectin as determined by the Receiver Operator Curves (ROC Curves), and the sensitivity and specificity of the individual biomarkers when comparing CXR+ pneumonia vs. URTI. Sensitivity (Sens) and Specifity (Spec) of the combination, along with the positive likelihood ratio (PLR), negative likelihood ration (NLR) positive predictive value (PPV) and negative predictive value (NPV) are shown.

TABLE 13

| | AUC* | Cutpoint** | Sens | Spec | PLR | NLR | PPV | NPV |
|---|---|---|---|---|---|---|---|---|
| CHI3L1 | 0.80 | >57.0 ng/mL | 93.3 | 66.1 | 2.8 | 0.1 | 15.2 | 99.3 |
| CRP | 0.87 | >31.4 ug/mL | 86.7 | 73.9 | 3.3 | 0.2 | 17.7 | 98.8 |
| PCT | 0.70 | >0.51 ng/mL | 70.0 | 65.6 | 2.0 | 0.5 | 11.7 | 97.1 |
| Pselectin | 0.62 | >59.2 ng/mL | 70.0 | 61.7 | 1.8 | 0.5 | 10.6 | 96.9 |

As in Example 15, additional classification and regression tree analysis (CRT) was performed to demonstrate a selection of biomarker combinations of the tested nine biomarkers. Table 14 show selected combination models chosen on the basis of varied input, and show the Sensitivity (Sens) and Specifity (Spec) of the combination, along with the positive likelihood ratio (PLR), negative likelihood ration (NLR) positive predictive value (PPV) and negative predictive value (NPV).

TABLE 14

| Model | Biomarkers entered | Other | Markers | Sens | Spec | PLR | NLR | PPV | NPV |
|---|---|---|---|---|---|---|---|---|---|
| 1 | All 9, continuous variables | Nodes: 20 parent, 10 child 5x misclassification cost** | CRP, CHI3L1 | 86.7 | 86.1 | 6.2 | 0.2 | 28.8 | 99.0 |
| 2 | All 9, continuous except dichotomized CRP, PCT* | Nodes: 20 parent, 10 child 5x misclassification cost** | CRP, CHI3L1 | 80.0 | 88.3 | 6.8 | 0.2 | 30.8 | 98.5 |

TABLE 14-continued

| Model | Biomarkers entered | Other | Markers | Sens | Spec | PLR | NLR | PPV | NPV |
|---|---|---|---|---|---|---|---|---|---|
| 3 | All 9, continuous except dichotomized CRP, PCT* | Nodes: 20 parent, 10 child 10x misclassification cost | CRP, CHI3L1 | 93.3 | 81.1 | 4.9 | 0.1 | 24.3 | 99.5 |
| 4 | All 9, continuous except dichotomized CRP, PCT* | Nodes: 10 parent, 5 child 5x misclassification cost | CRP, CHI3L1, IL18bpa | 80.0 | 91.1 | 9.0 | 0.2 | 36.9 | 98.6 |

*Dichotomized CRP (40 ug/mL) and PCT (0.5 ng/mL) because POC tests already exist at these cut-offs
**Misclassification costs always in favour of increased sensitivity for CXR+ pneumonia Example 17 Determining Whether Agnostic Biomarkers, Individually and in Combination are Able to Differentiate Between Individuals Having a Bacterial Infection which is Treatable with Antibiotics, and Individuals Having a Viral Infection for which Antibiotics are not Likely to be Effective A prospective study was done with a group of children (n=15) presenting to a community health facility in Africa with fever and upper respiratory tract symptoms. ELISA testing was done on the serum samples from these children using antibodies against the following panel of nine biomarkers selected from Table 1: CRP, PCT, sTie-2, Endoglin, P-selectin, vWF, CHI3L1, IL18bpa, and Ang3L1. The children were later identified as either (i) having bacteremia from one of *E. coli, S. aureus, S. flexneri, Salmonella, Streptococcus, H. Influenzae,* or *Acinetobacter* (n=16) or (ii) having a viral infection from one of Epstein Barr virus (EBV) Cytomegalovirus (CMV), Human herpes virus 6 (HHV6), parvovirus or mumps. Similar results were seen when the bacterial infections included *K. pneumonia* (data not shown).

Each biomarker was individually tested for its ability to discriminate between children having a bacterial infection which is treatable with antibiotics, and children having a viral infection that would not respond to antibiotics. The results of the bivariate analysis are shown in Table 15.

TABLE 15

| Biomarker | Cut-point (Youden) | Sensitivity (%) | Specificity (%) | PPV (%) | NPV (%) |
|---|---|---|---|---|---|
| Endoglin | <12.5 ng/mL | 73.3 | 75 | 65 | 81.6 |
| CHI3L1 | >29.8 ng/mL | 80 | 62.5 | 57.5 | 83.1 |
| CRP | >8.6 ug/mL | 93.3 | 68.7 | 65.4 | 99.4 |
| TREM1 | >71.1 pg/mL | 93.3 | 43.7 | 51.3 | 91.2 |
| PCT | >0.4 ng/mL | 60 | 100 | 100 | 79.8 |
| P-selectin | >48.4 ng/mL | 86.7 | 75 | 68.7 | 89.9 |
| ANGL3 | >294.6 ng/mL | 80 | 75 | 67 | 86 |
| IP10 | <477.8 ng/mL | 66.7 | 81.2 | 69.3 | 79.4 |
| IL18bpaa | <25.5 ng/mL | 93.3 | 62.5 | 61.2 | 93.7 |

Combinations of the nine biomarker were tested for their ability to differentiate between children having bacterial infections (treatable with antibiotics) and children having viral infections (not benefiting from antibiotics) by applying classification and regression tree analysis (CRT). For each biomarker, a point was assigned if the value of the biomarker was above the set cut-point (as determined using Youden Index). The sum of all the points was calculated to determine the "biomarker score". Table 16 show selected combination models chosen on the basis of the optimal score cut-point. The Sensitivity (Sens) and Specificity (Spec) of the combination, along with positive predictive value (PPV) and negative predictive value (NPV) are shown.

TABLE 16

| Combination | Cut-point (Youden) | Sensitivity (%) | Specificity (%) | PPV (%) | NPV (%) |
|---|---|---|---|---|---|
| TREM1 + IL18bpa | Score 2 | 86.7 | 87.5 | 81.5 | 91.2 |
| PCT + END (or PCT + Psel) | Score ≥1 | 93.3 | 75 | 70.3 | 94.7 |
| PCT + ANGL3 | Score ≥1 | 100 | 75 | 71.7 | 100 |
| PCT + IP10 | Score ≥1 | 100 | 81.2 | 77.2 | 100 |
| End + PCT + IL18bpa | Score ≥2 | 93.3 | 93.7 | 90.4 | 95.7 |
| PCT + ANGL3 + IL18bpa | Score ≥2 | 100 | 87.5 | 83.5 | 100 |
| PCT + ANGL3 + IP10 | Score ≥2 | 93.3 | 100 | 100 | 95.9 |

What is claimed is:

1. A method of determining the likelihood of a test individual having a critical and/or life threatening response to malaria, said method comprising:
   (i) detecting and quantifying a level of each of three protein biomarkers in a sample from the test individual, wherein the test individual has not been diagnosed or differentially diagnosed as having the suspected illness, wherein said protein biomarkers are angiopoietin-2 (Ang-2), 10 kDa interferon gamma-induced protein (IP-10), and soluble intercellular adhesion molecule-1 (siCAM-1),
   (ii) utilizing the quantified levels of each said protein biomarkers from said sample in a classifier derived from testing said protein biomarkers in one or more control populations (iii) making a determination as to whether said individual is at an increased risk of the critical and/or life threatening response as a result of application of said classifier.

2. The method of claim 1, wherein said detecting and quantifying of step (i) utilizes one or more devices to transform the sample into data indicative of the levels of each of said three protein biomarkers which can be used in said classifier.

3. The method of claim 2, wherein said one or more devices is an enzyme linked immunoassay which is utilized so as to transform the sample into data.

4. The method of claim 1, wherein the determination of step (iii) is indicative of said individual requiring the application of a treatment protocol as a result of the increased risk identified.

5. The method of claim 4, wherein said individual is subjected to the treatment protocol.

6. The method of claim 1, wherein said classifier is derived using at least two control populations, a population of individuals having malaria, and not having a critical and/or life threatening response to said malaria and a population of individuals having malaria and having a critical and/or life threatening response to said malaria.

7. The method of claim 1, wherein said classifier is derived using at least two control populations, a population of individuals having malaria which can be critical and/or life threatening, and not having a critical and/or life threatening response to said malaria and a population of individuals having malaria which can be critical and/or life threatening, and having a critical and/or life threatening response to said malaria.

8. The method of claim 1, wherein said classifier is derived using at least two control populations, a population of individuals considered normal and a population of individuals having malaria which can be critical and/or life threatening, and having a critical and/or life threatening response to malaria.

9. A method of determining the likelihood of a test individual having a critical and/or life threatening response to malaria, said method comprising:
   (i) detecting and quantifying a level of each of three protein biomarkers in a sample from the test individual, wherein said protein biomarkers are angiopoietin-2 (Ang-2), 10 kDa interferon gamma-induced protein (IP-10), and, soluble intercellular adhesion molecule-1 (siCAM-1),
   (ii) comparing said quantified levels of said protein biomarkers to control levels of said protein biomarkers from a control population (iii) determining the differential levels for each biomarker in the comparison of step (ii) so as to make a determination as to whether said test individual is at an increased risk of having the critical and/or life threatening response to malaria.

10. The method of claim 9, wherein said detecting and quantifying of step (i) utilizes one or more devices to transform the sample into data indicative of the levels of each of said three protein biomarkers which can be used to compare to the control population.

11. The method of claim 10, wherein said one or more devices is an enzyme linked immunoassay which is utilized so as to transform the sample into data.

12. The method of claim 9, wherein the determination of step (iii) is indicative of said individual requiring the application of a treatment protocol as a result of the increased risk identified.

13. The method of claim 12, wherein said individual is subjected to the treatment protocol.

14. The method of claim 9, wherein said control population is a population of individuals having the critical and/or life threatening response to malaria.

15. The method of claim 9, wherein said control population is a population of individuals having malaria, wherein the individuals have not developed a critical and/or life threatening response to said malaria.

16. The method of claim 9, wherein said control population is a population of individuals having malaria, wherein the individuals have developed a critical and/or life threatening response to said malaria.

17. The method of claim 9, wherein said control population is a population of individuals who are normal.

18. The method of claim 9, wherein said control population is a population of individuals that do not have malaria which is critical and/or life threatening.

19. The method of claim 9, wherein said control population is a population of individuals wherein the members of the control population have malaria which is critical and/or life threatening.

20. A method of determining the likelihood of a test individual having a critical and/or life threatening response to malaria, said method comprising:
   (i) detecting and quantifying a level of each of three protein biomarkers in a sample from the test individual, wherein said protein biomarkers are angiopoietin-2 (Ang-2), 10 kDa interferon gamma-induced protein (IP-10), and soluble intercellular adhesion molecule-1 (siCAM-1),
   (ii) utilizing the quantified levels of each said protein biomarkers from said sample in a classifier derived from testing said protein biomarkers in one or more control populations (iii) making a determination as to whether said individual is at an increased risk of a life threatening response as a result of application of said classifier.

21. The method of claim 20, wherein said detecting and quantifying of step (i) utilizes one or more devices to transform the sample into data indicative of the levels of each of said three protein biomarkers which can be used in said classifier.

22. The method of claim 21, wherein said one or more devices is an enzyme linked immunoassay which is utilized so as to transform the sample into data.

23. The method of claim 20, wherein the determination of step (iii) is indicative of said individual requiring the application of a treatment protocol as a result of the increased risk identified.

24. The method of claim 23, wherein said individual is subjected to the treatment protocol.

25. The method of claim 20, wherein said classifier is derived using at least two control populations, a population of individuals having malaria, and not having a critical and/or life threatening response to said malaria and a population of individuals having malaria and having a critical and/or life threatening response to said malaria.

26. The method of claim 20, wherein said classifier is derived using at least two control populations, a population of individuals having malaria which can be critical and/or life threatening, and not having a critical and/or life threatening response to said malaria and a population of individuals having malaria which can be critical and/or life threatening, and having a critical and/or life threatening response to said malaria.

27. The method of claim 20, wherein said classifier is derived using at least two control populations, a population of individuals considered normal and a population of individuals having malaria which can be critical and/or life threatening, and having a critical and/or life threatening response to said malaria.

* * * * *